United States Patent
Patil et al.

(10) Patent No.: US 10,662,388 B2
(45) Date of Patent: May 26, 2020

(54) ESTER COMPOUNDS, LUBRICATING OIL COMPOSITIONS CONTAINING SAME AND PROCESSES FOR MAKING SAME

(71) Applicant: ExxonMobil Chemical Patents Inc., Baytown, TX (US)

(72) Inventors: Abhimanyu O. Patil, Westfield, NJ (US); Kyle G. Lewis, Houston, TX (US); Satish Bodige, Wayne, NJ (US); Stephen Zushma, Clinton, NJ (US)

(73) Assignee: ExxonMobil Chemical Patents Inc., Baytown, TX (US)

( * ) Notice: Subject to any disclaimer, the term of this patent is extended or adjusted under 35 U.S.C. 154(b) by 61 days.

(21) Appl. No.: 15/988,716

(22) Filed: May 24, 2018

(65) Prior Publication Data

US 2019/0062663 A1  Feb. 28, 2019

Related U.S. Application Data

(60) Provisional application No. 62/551,068, filed on Aug. 28, 2017.

(30) Foreign Application Priority Data

Oct. 30, 2017 (EP) .................... 17199079

(51) Int. Cl.
*C10M 129/70* (2006.01)
*C07C 69/612* (2006.01)
(Continued)

(52) U.S. Cl.
CPC ........... *C10M 129/70* (2013.01); *C07C 67/08* (2013.01); *C07C 69/14* (2013.01); *C07C 69/24* (2013.01);
(Continued)

(58) Field of Classification Search
CPC .......... C10M 129/70; C10M 2207/281; C10M 2207/2815; C10M 105/34; C07C 69/24;
(Continued)

(56) References Cited

U.S. PATENT DOCUMENTS 3,652,655 A  3/1972 Fenton
4,658,708 A  4/1987 Rastoin
(Continued)

FOREIGN PATENT DOCUMENTS

DE  19653829  6/1998
EP  1710225  10/2006
(Continued)

OTHER PUBLICATIONS

Birney at al., "Parallel Combinatorial Esterification A Simple Experiment for Use in the Second-Semester Organic Chemistry Laboratory," Journal of Chemical Education, 1999, vol. 76, No. 11, pp. 1560-1561.
(Continued)

*Primary Examiner* — Taiwo Oladapo

(57) ABSTRACT

This disclosure relates to ester compounds formed from gamma-branched aliphatic alcohols, lubricating oil base stocks comprising such ester compounds, lubricating oil compositions comprising such ester compounds, and method of making such base stocks. The lubricating oil base stocks comprising the ester compounds exhibit desirable lubricating properties such as polarity.

26 Claims, 3 Drawing Sheets

(51) Int. Cl.

| | | |
|---|---|---|
| *C07C 67/08* | (2006.01) | |
| *C07C 69/24* | (2006.01) | |
| *C07C 69/78* | (2006.01) | |
| *C10M 105/34* | (2006.01) | |
| *C07C 69/26* | (2006.01) | |
| *C07C 69/614* | (2006.01) | |
| *C07C 69/14* | (2006.01) | |

(52) U.S. Cl.
CPC ............ *C07C 69/26* (2013.01); *C07C 69/612* (2013.01); *C07C 69/614* (2013.01); *C07C 69/78* (2013.01); *C10M 105/34* (2013.01); *C10M 2207/281* (2013.01); *C10M 2207/2815* (2013.01); *C10N 2220/022* (2013.01); *C10N 2220/028* (2013.01); *C10N 2230/74* (2013.01); *C10N 2240/10* (2013.01)

(58) Field of Classification Search
CPC ....... C07C 67/08; C07C 69/612; C07C 69/78; C07C 69/614; C07C 69/26; C07C 69/14; C10N 2240/10; C10N 2230/74; C10N 2220/028; C10N 2220/022
See application file for complete search history.

(56) References Cited

U.S. PATENT DOCUMENTS

| | | |
|---|---|---|
| 4,973,788 A | 11/1990 | Lin et al. |
| 5,087,788 A | 2/1992 | Wu |
| 5,625,106 A | 4/1997 | Marks et al. |
| 6,235,924 B1 * | 5/2001 | McConnell ............. C07C 67/08 560/103 |
| 8,119,850 B2 | 2/2012 | Fujikawa et al. |
| 8,383,869 B2 | 2/2013 | De Kraker |
| 8,748,361 B2 | 6/2014 | Wu et al. |
| 9,312,491 B2 | 4/2016 | Eu et al. |
| 2006/0178460 A1 * | 8/2006 | Herault ............. B01D 19/0404 524/284 |
| 2016/0017105 A1 | 1/2016 | Wu et al. |
| 2016/0257901 A1 | 9/2016 | Narine et al. |
| 2017/0183595 A1 | 6/2017 | Ng et al. |
| 2018/0119045 A1 | 5/2018 | Patil et al. |

FOREIGN PATENT DOCUMENTS

| | | | |
|---|---|---|---|
| GB | 999725 | 7/1965 | |
| GB | 999725 A * | 7/1965 | ............. C07C 1/213 |
| JP | 2004-077791 | 3/2004 | |
| JP | 2004077791 A * | 3/2004 | |
| JP | 2005-298443 | 10/2005 | |
| WO | 2014/004776 | 1/2014 | |
| WO | 2017/036755 | 3/2017 | |
| WO | 2017/116900 | 7/2017 | |

OTHER PUBLICATIONS

Chen et al., "Graphene Oxide: An Efficient Acid Catalyst for the Cnstruction of Esters from Acids and Alcohols," Synlett, vol. 28, pp. 981-985.

U.S. Appl. No. 15/904,629, filed Feb. 26, 2018, Lewis et al.

* cited by examiner

ESTER COMPOUNDS, LUBRICATING OIL COMPOSITIONS CONTAINING SAME AND PROCESSES FOR MAKING SAME

PRIORITY CLAIM

This application claims the benefit of Provisional Application No. 62/551,068, filed Aug. 28, 2017 and European Application No. 17199079.9, filed Oct. 30, 2017, the disclosures of both of which are incorporated herein by reference in their entirety.

FIELD OF THE DISCLOSURE

This disclosure relates to esters compounds, lubricating oil base stocks, lubricating oil compositions, and methods of making them. In particular, this disclosure relates to ester compounds of gamma-branched alcohols, and lubricating oil base stocks and lubricating oil formulations comprising such ester compounds.

BACKGROUND OF THE DISCLOSURE

Lubricants in commercial use today are prepared from a variety of natural and synthetic base stocks admixed with various additive packages and solvents depending upon their intended application. The base stocks typically include mineral oils, polyalphaolefins (PAO), gas-to-liquid (GTL) base oils, silicone oils, phosphate esters, diesters, polyol esters, and the like.

A major trend for passenger car engine oils (PCEOs) is an overall improvement in quality as higher quality base stocks become more readily available. Typically the highest quality PCEO products are formulated with base stocks such as PAOs or GTL stocks admixed with various additive packages.

Polyalpha-olefins (PAOs) are important lube base stocks with many excellent lubricant properties, including high viscosity index (VI), low volatility and are available in various viscosity range (e.g., kinematic viscosity at 100° C. in the range of 2 to 300 cSt). However, PAOs are paraffinic hydrocarbons with low polarity. This low polarity leads to low solubility and dispersancy for polar additives or sludge generated during service. To compensate for this low polarity, lube formulators usually add one or multiple polar co-base stocks. Ester or alkylated naphthalene (AN) is usually present at 1 to 50 wt % levels in many finished lubricant formulations to increase the fluid polarity which improves the solubility of polar additives and sludge.

Therefore, there is a need for polar base stock fluids that provide appropriate solubility and dispersibility for polar additives or sludge generated during service of lubricating oils.

The present invention meets this and other needs.

SUMMARY OF THE DISCLOSURE

It has been found that esters of gamma-branched aliphatic alcohols (especially aliphatic alcohols) can be advantageously used as lubricating oil base stocks with desirable lubricating oil properties such as polarity.

A first aspect of the present disclosure relates to an ester compound having the following formula (F-I):

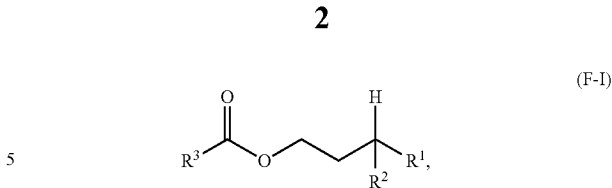

wherein $R^1$ and $R^2$ are independently each a C2 to C60 linear or branched alkyl group; and $R^3$ is a substituted or unsubstituted hydrocarbyl group.

A second aspect of the present disclosure relates to a lubricating oil composition comprising an ester compound of the first aspect of the present disclosure.

A third aspect of the present disclosure relates to a method for making a compound having formula (F-I) or a lubricating oil base stock comprising a compound having the following formula (F-I):

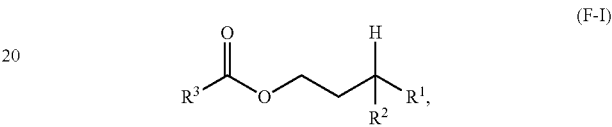

wherein $R^1$ and $R^2$ are independently each a C2 to C60 linear or branched alkyl group; and
$R^3$ is a substituted or unsubstituted hydrocarbyl group;
the method comprising:
reacting an acid having a formula (F-II) or an anhydride thereof having a formula (F-III) below with an alcohol having a formula (F-IV) below in the presence of an acid catalyst to obtain a reaction mixture:

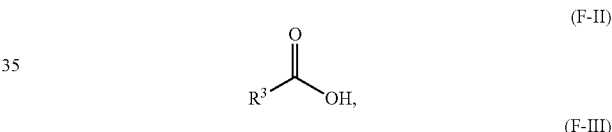

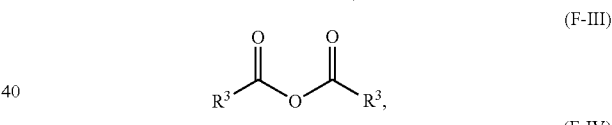

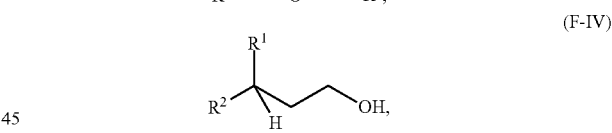

and
obtaining at least a portion of the compound or the lubricating oil base stock from the reaction mixture.

Further objects, features and advantages of the present disclosure will be understood by reference to the following drawings and detailed description.

DETAILED DESCRIPTION OF THE DISCLOSURE

Definitions

Figure 1:
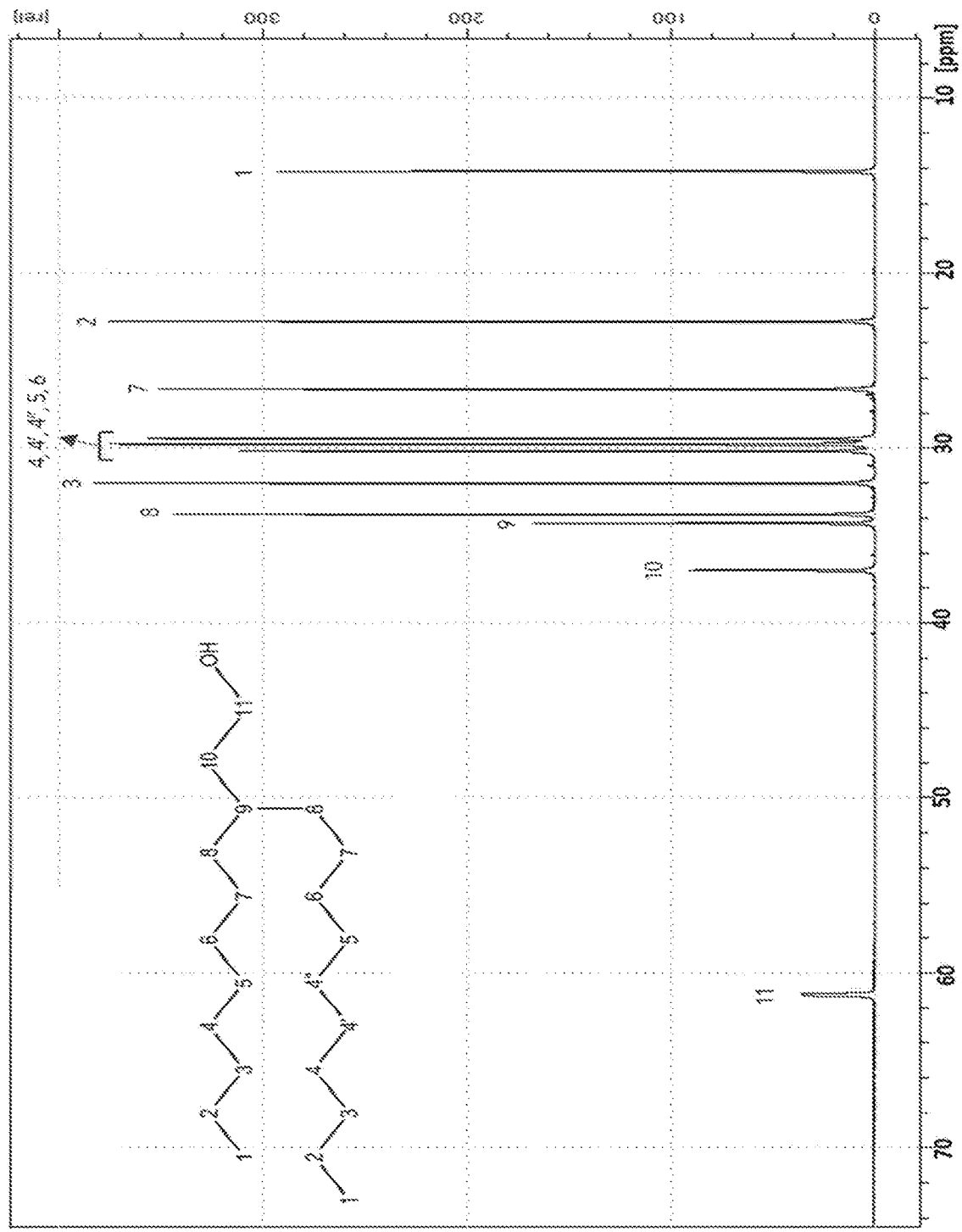
FIG. 1 is a $^{13}$C-NMR spectra of the C21-alcohol product made in Part A of the Examples in this disclosure.

In the present disclosure, the indefinite article "a" or "an" means at least one, unless it is clearly specified or indicated by the context to mean one.

"Alkyl group" refers to a saturated hydrocarbyl group consisting of carbon and hydrogen atoms. "Linear alkyl group" refers to a non-cyclic alkyl group in which all carbon atoms are covalently connected to no more than two carbon atoms. "Branched alkyl group" refers to a non-cyclic alkyl group in which at least one carbon atom is covalently connected to more than two carbon atoms. "Cycloalkyl group" refers to an alkyl group in which all carbon atoms form a ring structure.

"Aryl group" refers to an unsaturated, cyclic hydrocarbyl group consisting of carbon and hydrogen atoms in which the carbon atoms join to form a conjugated π system. Non-limiting examples of aryl groups include phenyl, 1-naphthyl, 2-naphthyl, 3-naphthyl, and the like.

"Arylalkyl group" refers to an alkyl group substituted by an aryl group or alkylaryl group. None-limiting examples of arylalkyl group include benzyl, 2-phenylpropyl, 4-phenylbutyl, 3-(3-methylphenyl)propyl, 3-(p-tolyl)propyl, and the like.

"Alkylaryl group" refers to an aryl group substituted by an alkyl group. Non-limiting examples of alkylaryl group include 2-methylphenyl, 3-methylphenyl, 4-methylphenyl, 2-methyl-1-naphtyl, 6-phenylhexyl, 5-pentylphenyl, 4-butylphenyl, 4-tert-butylphenyl, 4-octylphenyl, and the like.

"Cycloalkylalkyl group" refers to an alkyl group substituted by a cycloalkyl group or an alkylcycloalkyl group. An example of cycloalkylalkyl group is cyclohexylmethyl.

"Alkylcycloalkyl group" refers to a cycloalkyl group substituted by an alkyl group. Non-limiting examples of alkylcycloalkyl group include 2-methylcyclohexyl, 3-methylcyclohexyl, 4-methylcyclohexyl, 4-tert-butyl cyclohexyl, 4-phenylcyclohexyl, and the like.

"Hydrocarbyl group" refers to a group consisting of hydrogen and carbon atoms only. A hydrocarbyl group can be saturated or unsaturated, linear or branched, cyclic or acyclic, containing a cyclic structure or free of cyclic structure, and aromatic or non-aromatic.

"Cn" group or compound refers to a group or a compound comprising carbon atoms at total number thereof of n. Thus, "Cm-Cn" or "Cm to Cn" group or compound refers to a group or compound comprising carbon atoms at a total number thereof in the range from m to n. Thus, a C1-C50 alkyl group refers to an alkyl group comprising carbon atoms at a total number thereof in the range from 1 to 50.

"Mono-ester" refers to a compound having one ester (—C(O)—O—) functional group therein.

"Guerbet alcohol" refers to beta-substituted alcohol having a structure corresponding to the following formula:

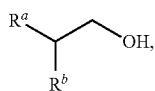

where $R^a$ and $R^b$ are independently linear, branched, cyclic, substituted or unsubstituted hydrocarbyl groups preferably comprising from c1 to c2 carbon atoms, where c1 and c2 can be, independently, 1, 2, 3, 4, 5, 6, 7, 8, 9, 10, 15, 20, 25, 30, 35, 40, 45, 50, 55, 60, 65, 70, 75, 80, 85, 90, 95, 100, as long as c1<c2. More preferably c1=2 and c2=50. Preferably $R^a$ and $R^b$ are alkyl groups. More preferably $R^a$ and $R^b$ are linear or branched alkyl groups.

"Gamma-branched alcohol" refers to an alcohol having a structure corresponding to the following formula:

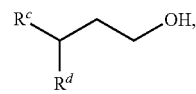

where $R^c$ and $R^d$ are independently linear, branched, cyclic, substituted or unsubstituted hydrocarbyl groups preferably comprising from d1 to d2 carbon atoms, where d1 and d2 can be, independently, 1, 2, 3, 4, 5, 6, 7, 8, 9, 10, 15, 20, 25, 30, 35, 40, 45, 50, 55, 60, 65, 70, 75, 80, 85, 90, 95, 100, as long as d1<d2. More preferably d1=2 and d2=50. Preferably $R^c$ and $R^d$ are alkyl groups. More preferably $R^c$ and $R^d$ are linear or branched alkyl groups. Still more preferably $R^c$ and $R^d$ differ in terms of total number of carbon atoms contained therein by two (2).

"SAE" refers to SAE International, formerly known as Society of Automotive Engineers, which is a professional organization that sets standards for internal combustion engine lubricating oils.

"SAE J300" refers to the viscosity grade classification system of engine lubricating oils established by SAE, which defines the limits of the classifications in rheological terms only.

"Lubricating oil" refers to a substance that can be introduced between two or more surfaces and lowers the level of friction between two adjacent surfaces moving relative to each other. A lubricating oil "base stock" is a material, typically a fluid at various levels of viscosity at the operating temperature of the lubricating oil, used to formulate a lubricating oil by admixing with other components. Non-limiting examples of base stocks suitable in lubricating oils include API Group I, Group II, Group III, Group IV, and Group V base stocks. If one base stock is designated as a primary base stock in the lubricating oil, any additional base stock may be called a co-base stock.

All kinematic viscosity values in the present disclosure are as determined pursuant to ASTM D445. Kinematic viscosity at 100° C. is reported herein as KV100, and kinematic viscosity at 40° C. is reported herein as KV40. Unit of all KV100 and KV40 values herein is cSt unless otherwise specified.

All viscosity index ("VI") values in the present disclosure are as determined pursuant to ASTM D2270.

All Noack volatility ("NV") values in the present disclosure are as determined pursuant to ASTM D5800 unless specified otherwise. Unit of all NV values is wt %, unless otherwise specified.

All percentages in describing chemical compositions herein are by weight unless specified otherwise. "wt %" means percent by weight.

"Consisting essentially of" means comprising at a concentration by weight of at least 90 wt %, based on the total weight of the mixture in question. Thus, a lubricating oil base stock consisting essentially of a given ester compound comprises that ester compound at a concentration by weight of at least 90 wt %, based on the total weight of the lubricating oil base stock.

All numerical values within the detailed description and the claims herein are modified by "about" or "approximately" the indicated value, taking into account experimental error and variations that would be expected by a person having ordinary skill in the art.

I. The Gamma-Branched Alcohol-Derived Ester Compounds

One aspect of the present disclosure is a novel category of compounds having a general formula (F-I) below:

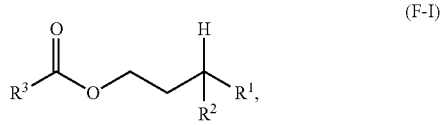

(F-I)

wherein $R^1$ and $R^2$ are independently each a hydrocarbyl group comprising at least 2 carbon atoms therein (preferably a C2 to C60 hydrocarbyl group, more preferably a C2 to C60 alkyl group, still more preferably a C2 to C60 linear or branched alkyl group, still more preferably a C2 to C30 linear or branched alkyl group); and $R^3$ is a hydrocarbyl group. To the extent this compound can be considered as an ester derived from a gamma-branched alcohol, it will be referred to as such in the present disclosure, and it is also referred to as "ester of the present disclosure" herein.

Preferably $R^1$ and $R^2$ each independently comprise c1 to c2 carbon atoms, where c1 and c2 can be, independently, any integer from 2 to 60, such as 2, 3, 4, 5, 6, 7, 8, 9, 10, 12, 14, 16, 18, 20, 22, 24, 26, 28, 30, 32, 34, 36, 38, 40, 42, 44, 46, 48, 50, 52, 54, 56, 58, or 60, as long as c1<c2. Preferably c1=2 and c2=30. More preferably c1=2 and c2=24. Still more preferably c1=4, and c2=16. Still more preferably c1=4, and c2=12. Preferably $R^1$ and $R^2$ each independently comprise even number of carbon atoms.

At least one of $R^1$ and $R^2$ (preferably both $R^1$ and $R^2$ independently each) can be a branched alkyl group, preferably a branched alkyl group having the following formula (F-IV):

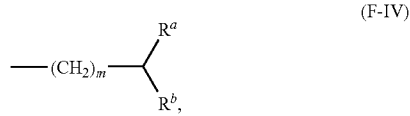

(F-IV)

where $R^a$ and $R^b$ are independently hydrocarbyl groups, preferably alkyl groups, more preferably linear or branched alkyl groups, still more preferably linear alkyl groups, m is a non-negative integer, preferably m≥2, more preferably m≥3, still more preferably m≥4, still more preferably m≥5, still more preferably m≥6, still more preferably m≥7. Preferably $R^a$ and $R^b$ each independently comprise c3 to c4 carbon atoms, where c3 and c4 can be, independently, any integer from 1 to 57, such as 1, 2, 3, 4, 5, 6, 7, 8, 9, 10, 12, 14, 16, 18, 20, 22, 23, 24, 26, 28, 30, 32, 34, 36, 38, 40, 42, 44, 46, 48, 50, 52, 54, 56, or 57, as long as c3<c4. More preferably c3=1 and c4=50. Still more preferably c3=1 and c4=40. Still more preferably c3=1 and c4=20. Still more preferably c3=1 and c4=16. Still more preferably c3=1, and c4=10. In one specific embodiment, m=0 and $R^1$ and/or $R^2$ can be a group branched at the 1-location, i.e., the carbon directly connected to the quaternary carbon atom. Non-limiting examples of branched alkyls for $R^1$ and $R^2$ include: 2-ethylhexyl, 2-propylheptanyl, 2-butyloctyl, and 3,5-dimethyloctyl.

At least one of $R^1$ and $R^2$ (preferably both $R^1$ and $R^2$ independently) can be linear alkyl groups such as: ethyl, n-propyl, n-butyl, n-pentyl, n-hexyl, n-heptyl, n-octyl, n-nonyl, n-decyl, n-undecyl, n-dodecyl, n-tridecyl, n-tetradecyl, n-pentadecyl, n-hexadecyl, n-heptadecyl, n-octadecyl, n-nonadecyl, n-icosyl, n-henicosyl, n-docosyl, n-tricosyl, n-tetracosyl, n-pentacosyl, n-hexacosyl, n-octacosyl, and n-triacontyl. Preferably, the total number of carbon atoms in linear $R^1$ and $R^2$ is an even number. Preferably, the total number of carbon atoms in the linear $R^1$ and/or $R^2$ combined is from a1 to a2, where a1 and a2 can be, independently, 8, 10, 12, 14, 16, 18, 20, 22, 24, 26, 28, 30, 32, 34, 36, 38, 40, 42, 44, 46, 48, 52, 56, 60, 64, 80, 96, or 100, as long as a1<a2. Preferably the total number of carbon atoms in the linear $R^1$ and $R^2$ combined is from 8 to 96, more preferably from 8 to 80, still more preferably from 8 to 64, still more preferably from 8 to 48, still more preferably from 8 to 40, still more preferably from 8 to 32, still more preferably from 8 to 28, still more preferably from 8 to 26, still more preferably from 8 to 24, still more preferably from 8 to 22, and still more preferably from 8 to 20.

Preferably, the total number of carbon atoms in $R^1$ and $R^2$ combined is from b1 to b2, where b1 and b2 can be, independently, 8, 10, 12, 14, 16, 18, 20, 22, 24, 26, 28, 30, 32, 34, 36, 38, 40, 42, 44, 46, 48, 52, 56, 60, 64, 80, 96, or 100, as long as b1<b2. Preferably the total number of carbon atoms in $R^1$ and $R^2$ is in a range from 8 to 96, more preferably from 8 to 80, still more preferably from 8 to 64, still more preferably from 8 to 48, still more preferably from 8 to 40, still more preferably from 8 to 32, still more preferably from 8 to 28, still more preferably from 8 to 26, still more preferably from 8 to 24, still more preferably from 8 to 22, and still more preferably from 8 to 20.

Preferably the difference in carbon numbers contained $R^1$ and $R^2$ is two (2). In such case, it is particularly preferred that both $R^1$ and $R^2$ contain even number of carbon atoms. Thus, one of $R^1$ and $R^2$ preferably contains 4, 6, 8, 10, 12, 14, 16, 18, 20, 22, 24, 26, 28, 30, 32, 34, 36, 38, 40, 42, 44, 46, 48, 50, 52, 54, 56, or 58 carbon atoms, and the other contains two more carbon atoms. Still more preferably, one of $R^1$ and $R^2$ comprises 6, 8, 10, 12, 14, 16, 18, 20, 22, 24, 26, or 28 carbon atoms, and the other comprises two more carbon atoms. More preferably, $R^2$ is identical to $R^1$—$CH_2$—$CH_2$—.

$R^3$ can be any substituted or unsubstituted hydrocarbyl group. $R^3$ can preferably comprise up to 60, 50, 40, 30, or 20 carbon atoms. Preferably $R^3$ is a C1-C24 group comprising carbon atoms at a number in the range from c1 to c2, where c1 and c2 can be, independently, 1, 2, 3, 4, 5, 6, 7, 8, 9, 10, 11, 12, 13, 14, 15, 16, 17, 18, 19, 20, 21, 22, 23, or 24, as long as c1<c2. Preferably, $R^3$ is a group selected from (a) linear or branched alkyl group, alkylaryl group, aryl group, arylalkyl group, cycloalkyl group, alkylcycloalkyl group, and cycloalkylalkyl group; and (b) substituted derivatives of those in category (a). Substitution to the category (a) hydrocarbyl groups include, but are not limited to: oxygen-containing groups such as alkoxy groups, nitrogen-containing groups, and the like.

$R^3$ can be preferably an alkyl group, an aryl group, an arylalkyl group, an alkylaryl group, a cycloalkyl group, a cycloalkylalkyl group, or an alkylcycloalkyl group.

Non-limiting examples of $R^3$ as an alkyl group include C1-C24 linear or branched alkyl groups such as methyl, ethyl, n-propyl, n-butyl, n-pentyl, n-hexyl, n-heptyl, n-octyl, n-nonyl, n-decyl, n-undecyl, n-dodecyl, n-tridecyl, n-tetradecyl, n-pentadecyl, n-hexadecyl, n-heptadecyl, n-octadecyl, n-nonadecyl, n-icosyl, n-henicosyl, n-docosyl, n-tricosyl, n-tetracosyl, and branched isomeric groups thereof, and the like.

Non-limiting examples of $R^3$ as an aryl group include phenyl, all naphthyls, all phenanthyls, all indenyls, and the like.

Non-limiting examples of $R^3$ as an alkylaryl group include alkyl-substituted phenyls, alkyl-substituted naphtyls, and alkyl substituted phenanthryls. Particular mention can be made of those phenyl groups substituted by an alkyl group such as o, p, and m-methylphenyls, o, p, and m-ethylphenyls, o, p, and m-n-propylphenyls, o, p, and m-n-butylphenyls, o, p, and m-n-pentylphenyls, o, p, and m-n-hexylphenyls, o, p, and m-n-heptylphenyls, o, p, and m-n-octylphenyls, o, p, and m-n-nonylphenyls, o, p, and m-n-decylphenyls, o, p, and m-n-undecylphenyls, o, p, and m-n-dodecylphenyls, o, p, and m-n-tridecylphenyls, o, p, and m-n-tetradecylphenyls, o, p, and m-n-pentadecylphenyls, o, p, and m-n-hexadecylphenyls, o, p, and m-n-heptadecylphenyls, o, p, and m-n-octadecylphenyls; o, p, and m-1-methylmethylphenyls, o, p, and m-1-methylethylphenyls, o, p, and m-1-methylpropylphenyls, o, p, and m-1-methylbutylphenyls, o, p, and m-1-methylpentylphenyls, o, p, and m-1-methylhexylphenyls, o, p, and m-1-methylheptylphenyls, o, p, and m-1-methyloctylphenyls, o, p, and m-1-methylnonylphenyls, o, p, and m-1-methyldecylphenyls, o, p, and m-1-methylundecylphenyls, o, p, and m-1-methyldodecylphenyls, o, p, and m-1-methyltridecylphenyls, o, p, and m-1-methyltetradecylphenyls, o, p, and m-1-methylpentadecylphenyls, o, p, and m-1-methylhexadecylphenyls, o, p, and m-1-methylheptadecylphenyls, and o, p, and m-1-methyloctadecylphenyls.

Non-limiting examples of $R^3$ as an arylalkyl group include: benzyl, 2-phenylethyl, 3-phenylpropyl, 4-phenylbutyl, 5-phenylpentyl, 6-phenylhexyl, 7-phenylheptyl, 8-phenyloctyl, 9-phenylnonyl, and 10-phenyldecyl, and the like.

Preferred examples of aromatic $R^3$ groups are: phenyl, benzyl, 2-phenylethyl, 3-phenylpropryl, 4-phenylbutyl, 3-(3-methylphenyl)propyl, 3-(p-tolyl)propyl, 2-methylphenyl, 3-methylphenyl, 4-methylphenyl, 2-methyl-1-naphthyl, 6-phenylhexyl, 5-pentylphenyl, 4-butylphenyl, 4-tert-butylphenyl, 7-phenylheptanyl, 4-octylphenyl, 2-methylcyclohexyl, 3-methylcyclohexyl, 4-methylcyclohexyl, 4-tert-butyl cyclohexyl, 4-phenylcyclohexyl, cyclohexylpentyl, nitrophenylmethyl, xylylmethyl, xylylpropyl, methoxyphenylethyl, methoxyphenylpropyl, methoxyphenylbutyl, nitrophenylpropyl, nitrophenylbutyl, and xylylbutyl.

Particularly desirable examples of the ester compounds of the present disclosure are as follows: 3-ethylheptyl acetate; 3-ethylheptyl propanoate; 3-ethylheptyl butanoate; 3-ethylheptyl pentanoate; 3-ethylheptyl hexanoate; 3-ethylheptyl octanoate; 3-ethylheptyl decanoate; 3-ethylheptyl dodecanoate; 3-ethylheptyl tetradecanoate; 3-ethylheptyl hexadecanoate; 3-ethylheptyl octadecanoate; 3-ethylheptyl icosanoate; 3-ethylheptyl 3-phenylpropanoate; 3-ethylheptyl 2-phenylacetate; 3-ethylheptyl benzoate; 3-butylnonyl acetate; 3-butylnonyl propanoate; 3-ethylheptyl acetate; 3-propyloctyl propanoate; 3-propyloctyl butanoate; 3-propyloctyl pentanoate; 3-propyloctyl hexanoate; 3-propyloctyl octanoate; 3-propyloctyl decanoate; 3-propyloctyl dodecanoate; 3-propyloctyl tetradecanoate; 3-propyloctyl hexadecanoate; 3-propyloctyl octadecanoate; 3-propyloctyl icosanoate; 3-propyloctyl 3-phenylpropanoate; 3-propyloctyl 2-phenylacetate; 3-propyloctyl benzoate; 3-butylnonyl butanoate; 3-butylnonyl pentanoate; 3-butylnonyl hexanoate; 3-butylnonyl octanoate; 3-butylnonyl decanoate; 3-butylnonyl dodecanoate; 3-butylnonyl tetradecanoate; 3-butylnonyl hexadecanoate; 3-butylnonyl octadecanoate; 3-butylnonyl icosanoate; 3-butylnonyl 3-phenylpropanoate; 3-butylnonyl 2-phenyl acetate; 3-butylnonyl benzoate; 3-hexylundecyl acetate; 3-hexylundecyl propanoate; 3-hexylundecyl butanoate; 3-hexylundecyl pentanoate; 3-hexylundecyl hexanoate; 3-hexylundecyl octanoate; 3-hexylundecyl decanoate; 3-hexylundecyl dodecanoate; 3-hexylundecyl tetradecanoate; 3-hexylundecyl hexadecanoate; 3-hexylundecyl octadecanoate; 3-hexylundecyl icosanoate; 3-hexylundecyl 3-phenylpropanoate; 3-hexylundecyl 2-phenylacetate; 3-hexylundecyl benzoate; 3-octyltridecyl acetate; 3-octyltridecyl propanoate; 3-octyltridecyl butanoate; 3-octyltridecyl pentanoate; 3-octyltridecyl hexanoate; 3-octyltridecyl octanoate; 3-octyltridecyl decanoate; 3-octyltridecyl dodecanoate; 3-octyltridecyl tetradecanoate; 3-octyltridecyl hexadecanoate; 3-octyltridecyl octadecanoate; 3-octyltridecyl icosanoate; 3-octyltridecyl 3-phenylpropanoate; 3-octyltridecyl 2-phenylacetate; 3-octyltridecyl benzoate; 3-decylpentadecyl acetate; 3-decylpentadecyl propanoate; 3-decylpentadecyl butanoate; 3-decylpentadecyl pentanoate; 3-decylpentadecyl hexanoate; 3-decylpentadecyl octanoate; 3-decylpentadecyl decanoate; 3-decylpentadecyl dodecanoate; 3-decylpentadecyl tetradecanoate; 3-decylpentadecyl hexadecanoate; 3-decylpentadecyl octadecanoate; 3-decylpentadecyl icosanoate; 3-decylpentadecyl 3-phenylpropanoate; 3-decylpentadecyl 2-phenylacetate; 3-decylpentadecyl benzoate; 3-dodecylheptadecyl acetate; 3-dodecylheptadecyl propanoate; 3-dodecylheptadecyl butanoate; 3-dodecylheptadecyl pentanoate; 3-dodecylheptadecyl hexanoate; 3-dodecylheptadecyl octanoate; 3-dodecylheptadecyl decanoate; 3-dodecylheptadecyl dodecanoate; 3-dodecylheptadecyl tetradecanoate; 3-dodecylheptadecyl hexadecanoate; 3-dodecylheptadecyl octadecanoate; 3-dodecylheptadecyl icosanoate; 3-dodecylheptadecyl 3-phenylpropanoate; 3-dodecylheptadecyl 2-phenylacetate; and 3-dodecylheptadecyl benzoate.

II. The Lubricating Oil Composition Comprising Ester of the Present Disclosure

II. 1 General

The esters of the present disclosure are useful as base stocks in formulating lubricating oils. The oil composition of the present disclosure summarized above can be a portion or the entirety of a lubricating oil formulation product. Thus, the oil composition can be: (i) a base stock; (ii) a mixture of a first base stock and the remainder of the formulation absent the first base stock; (ii) a mixture of a first base stock with one or more other base stocks contained in the lubricating oil formulation absent the additive components in the lubricating oil formulation; (iii) a mixture of a first base stock and all other base stocks contained in the lubricating oil formulation but absent any additive components that may be present in the lubricating oil formulation; (iv) a mixture of the first base stock and one or more other base stocks, but not all the other base stocks, contained in the lubricating oil formulation, and at least a portion of the additive components contained in the lubricating oil formulation; and (v) a mixture of the first base stock and all additive components contained in the lubricating oil formulation, but no other base stocks contained in the lubricating oil formulation.

II. 2 Lubricating Oil Base Stocks Comprising Gamma-Branched Alcohol-Derived Ester The esters of gamma-branched alcohols of the present disclosure have desirable properties such as KV100, KV40, and viscosity index comparable to certain commercial Group V ester-type base stocks. The high polarity of the gamma-branched alcohol-derived ester molecules as a result of the presence of the ester group lends them excellent blending capabilities with many other base stocks, providing needed solvency and dispersancy of polar components such as additives and sludge formed during the service life of the lubricating oil.

The lubricating oil base stock of the present disclosure can comprise a single gamma-branched alcohol-derived ester compound as disclosed above. The purity of the ester compound can be, e.g., at least 80, 90, 95, 98, or even 99 wt %, based on the total weight of the base stock.

The lubricating oil base stock of the present disclosure can comprise two or more gamma-branched alcohol-derived esters as disclosed above. Such base stock can be produced by mixing two ester compound in their substantially pure form, or produced from a single esterification reaction operation by reacting (i) one or more acid(s) with two or more gamma-branched alcohols, or (ii) two or more acids with one or more gamma-branched alcohols. Such mixed-ester base stock can be particularly advantageous where a mixture of gamma-branched alcohols can be procured at a lower cost than a pure single-compound gamma-branched alcohol.

The lubricating oil base stock of the present disclosure desirably has a KV100 in the range from k1 to k2 cSt, where k1 and k2 can be, independently, 1.0, 1.2, 1.4, 1.5, 1.6, 1.8, 2.0, 2.2, 2.4, 2.5, 2.6, 2.8, 3.0, 3.2, 3.4, 3.5, 3.6, 3.8, 4.0, 4.5, 5.0, 5.5, 6.0, 6.5, 7.0, 7.5, 8.0, 8.5, 9.0, 9.5, 10.0, 10.5, 11.0, 11.5, 12.0, 12.5, 13.0, 13.5, 14.0, 14.5, 15.0, 15.5, 16.0, 16.5, 17.0, 17.5, 18.0, 18.5, 19.0, 19.5, 20.0, 20.5, 21.0, 21.5, 22.0, 22.5, 23.0, 23.5, 24.0, 24.5, 25.0, 25.5, 26.0, 26.5, 27.0, 27.5, 28.0, 28.5, 29.0, 29.5, 30.0, 30.5, 31.0, 31.5, 32.0, 32.5, 33.0, 33.5, 34.0, 34.5, 35.0, 35.5, 36.0, 36.5, 37.0, 37.5, 38.0, 38.5, 39.0, 39.5, 40.0, as long as k1<k2. Preferably k1=4.0, and k2=30.0. More preferably k1=5.0, and k2=25.0. Therefore, the base stock of the present disclosure has a relatively "low" viscosity at the normal operating temperature of an internal combustion engine lubricating oil.

The lubricating oil base stock of the present disclosure desirably has a viscosity index as determined pursuant to ASTM D2270 in the range from v1 to v2, where v1 and v2 can be, independently, −100, −90, −80, −70, −60, −50, −40, −30, −20, −10, 0, 10, 20, 30, 40, 50, 60, 70, 80, 90, 100, 110, 120, 130, 140, 150, 160, 170, 180, 190, 200, 210, 220, 230, 240, 250, 260, 270, 290, or 300, as long as v1<v2. Preferably v1=0, and v2=250. More preferably v1=25, and v2=200. Still more preferably v1=100, and v2=170.

The base stock of the present disclosure desirably has a NV value in the range from n1 to n2 wt %, where n1 and n2 can be, independently, 0, 0.1, 0.5, 1, 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, or 90, as long as n1<n2. Preferably n1=0 and n2=50. More preferably n1=0 and n2=30. Still more preferably n1=0 and n2=20. Still more preferably n1=0 and n2=16. In general, for the same type of gamma-branched alcohol-derived ester base stock, the larger the molecular weight of the molecule, the lower the NV value. For engine oils and base stocks for them, typically a low NV value is preferred, all other parameters held equal.

The base stock of the present disclosure desirably have an aniline value as determined by ASTM D611 of no higher than 30, 25, 20, or 15.

Guerbet alcohols-derived esters are known as good quality lubricating oil base stocks. In a surprising manner, it has been found that base stocks of the present disclosure based on gamma-branched alcohol-derived esters perform better than Guerbet alcohols-derived ester base stocks having at the same molecular weight and with comparable molecular structure. In particular, it has been found that the ester base stocks of the present disclosure tend to have lower viscosity (KV100, in particular) and/or lower volatility (NV value, in particular).

Moreover, compared to PAO base stocks at similar viscosity (KV100, in particular), the base stock of the present disclosure comprising a gamma-branched alcohol-derived ester tend to have higher polarity and lower volatility (NV value, in particular).

The gamma-branched alcohol-derived ester base stock of the present disclosure can be used as a primary base stock or a co-base stock in any lubricating oil formulation. Preferably, the gamma-branched alcohol-derived ester base stock of the present disclosure is used as a co-base stock in conjunction with a second base stock designated as a primary base stock. In certain applications, it may be desirable to include two or even more additional base stocks in the lubricating oil formulation, in addition to the gamma-branched alcohol-derived ester base stock of the present disclosure. For the convenience of description, the gamma-branched alcohol-derived ester base stock is merely referred to as a generic base stock herein, regardless of its primary base stock or co-base stock designation. The base stock of the present disclosure comprising a gamma-alcohol-derived ester can be particularly advantageous when used as a co-base stock with a non-polar base stock such as those Group I, II, III, GTL, and Group IV base stocks.

The gamma-branched alcohol-derived ester base stocks of the present disclosure are preferably used for formulating automobile engine lubricating oils, preferably those meeting the SAE J300 classification standards. However, it is contemplated that the base stocks of the present disclosure may be used to formulate other lubricating oils (e.g., automobile drive-line oils, industrial lubricating oils, gear oils, greases, and the like), heat transfer oils (e.g., transformer oils), hydraulic power transfer oils, processing oils, and the like.

III. Method for Making the Ester Compounds and Lubricating Oil Base Stock Comprising the Same One aspect of the present disclosure relates to a process for making (i) a compound having the following formula (F-I), and/or (ii) a lubricating oil base stock comprising a compound having the following formula (F-I):

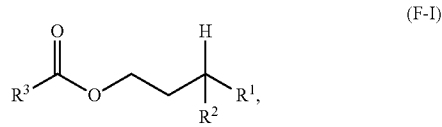

(F-I)

wherein $R^1$ and $R^2$ are independently each a C2 to C30 linear or branched alkyl group;
$R^3$ is a hydrocarbyl group;
the method comprising:
reacting an acid having a formula (F-II) or an anhydride thereof having a formula (F-III) below with an alcohol having a formula (F-IV) below in the presence of an acid catalyst to obtain a reaction mixture:

(F-II)

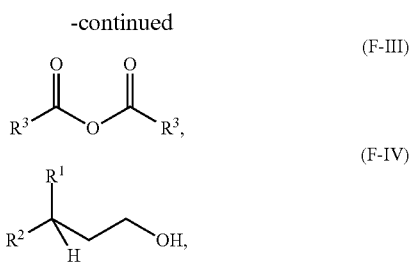

(F-III)

(F-IV)

and obtaining the compound from the reaction mixture.

It is highly desirable that the acid/anhydride used in the reaction are those of a single mono-acid for both the purpose of making a single compound having formula (F-I) or a lubricating oil base stock comprising a compound having formula (F-I), although those of multiple acids can be used as well, especially for the purpose of making a lubricating oil base stock which can comprise a mixture of multiple, different compounds having a molecular structure represented by formula (F-I).

In the acid or anhydride, $R^3$ can be any hydrocarbyl group. Preferably $R^3$ is a C1-C24 group comprising carbon atoms at a number in the range from c1 to c2, where c1 and c2 can be, independently, 1, 2, 3, 4, 5, 6, 7, 8, 9, 10, 11, 12, 13, 14, 15, 16, 17, 18, 19, 20, 21, 22, 23, or 24, as long as c1<c2. Such $R^3$ can be preferably an alkyl group, an aryl group, an arylalkyl group, an alkylaryl group, a cycloalkyl group, a cycloalkylalkyl group, or an alkylcycloalkyl group.

Non-limiting examples of $R^3$ as an alkyl group in the formulae of the acid and/or anhydride include C1-C24 linear or branched alkyl groups such as methyl, ethyl, n-propyl, n-butyl, n-pentyl, n-hexyl, n-heptyl, n-octyl, n-nonyl, n-decyl, n-undecyl, n-dodecyl, n-tridecyl, n-tetradecyl, n-pentadecyl, n-hexadecyl, n-heptadecyl, n-octadecyl, n-nonadecyl, n-icosyl, n-henicosyl, n-docosyl, n-tricosyl, n-tetracosyl, and branched isomeric groups thereof.

Non-limiting examples of $R^3$ as an aryl group in the formulae of the acid and anhydride include phenyl, all naphthyls, all phenanthryls, all indenyls, and the like.

None-limiting examples of $R^3$ as an alkylaryl group in the formulae of the acid and anhydride include alkyl-substituted phenyls, alkyl-substituted naphthyls, and alkyl substituted phenanthryls. Particular mention can be made of those phenyl groups substituted by an alkyl group such as o, p, and m-methylphenyls, o, p, and m-ethylphenyls, o, p, and m-n-propylphenyls, o, p, and m-n-butylphenyls, o, p, and m-n-pentylphenyls, o, p, and m-n-hexylphenyls, o, p, and m-n-heptylphenyls, o, p, and m-n-octylphenyls, o, p, and m-n-nonylphenyls, o, p, and m-n-decylphenyls, o, p, and m-n-undecylphenyls, o, p, and m-n-dodecylphenyls, o, p, and m-n-tridecylphenyls, o, p, and m-n-tetradecylphenyls, o, p, and m-n-pentadecylphenyls, o, p, and m-n-hexadecylphenyls, o, p, and m-n-heptadecylphenyls, o, p, and m-n-octadecylphenyls; o, p, and m-1-methylmethylphenyls, o, p, and m-1-methylethylphenyls, o, p, and m-1-methylpropylphenyls, o, p, and m-1-methylbutylphenyls, o, p, and m-1-methylpentylphenyls, o, p, and m-1-methylhexylphenyls, o, p, and m o, p, and m-1-methylheptylphenyls, o, p, and m-1-methyloctylphenyls, o, p, and m-1-methylnonylphenyls, o, p, and m-1-methyldecylphenyls, o, p, and m-1-methylundecylphenyls, o, p, and m-1-methyldodecylphenyls, o, p, and m-1-methyltridecylphenyls, o, p, and m-1-methyltetradecylphenyls, o, p, and m-1-methylpentadecylphenyls, o, p, and m-1-methylhexadecylphenyls, o, p, and m-1-methylheptadecylphenyls, and o, p, and m-1-methyloctadecylphenyls.

None-limiting examples of $R^3$ as an arylalkyl group in the formulae of the acid and/or anhydride include: benzyl, 2-phenylethyl, 3-phenylpropyl, 4-phenylbutyl, 5-phenylpentyl, 6-phenylhexyl, 7-phenylheptyl, 8-phenyloctyl, 9-phenylnonyl, and 10-phenyldecyl.

Particularly desirable examples of the acid and anhydride useful in the process of the present disclosure are as follows: acetic acid; propanoic acid; butanoic acid; pentanoic acid; hexanoic acid; heptanoic acid; octanoic acid; nonanoic acid; decanoic acid; undecanoic acid; dodecanoic acid; tridecanoic acid; tetradecanoic acid; pentadecanoic acid; hexadecanoic acid; heptadecanoic acid; octodecanoic acid; nonadecanoic acid; icosanoic acid; benzoic acid; 2-phenylacetic acid; 3-phenylpropanoic acid; 4-phenylbutanoic acid; 5-phenylpentanoic acid; 6-phenylhexanoic acid; 7-phenylheptanoic acid; 8-phenyloctanoic acid; 9-phenylnonaoic acid; 10-phenyldecanoic acid; and anhydrides of the above acids.

It is highly desirable that a single alcohol having formula (F-IV) is used in the esterification reaction to produce a single ester of the present disclosure and/or a lubricating oil base stock comprising an ester of the present disclosure. In such case, if an acid/anhydride of a single mono-acid is used, a high-purity ester compound having a formula (F-I) can be obtained and used as a lubricating oil base stock. This is illustrated in Examples B1, B2, B3, B4, B5, and B6 in the present disclosure.

It is also contemplated that multiple alcohols can be used in the esterification reaction. In the case where two different alcohols and the acid/anhydride of a single mono-acid are used in the reaction, the reaction mixture will comprise two different ester compounds. The ratio between the quantities of the two ester compounds can change as a function of the ratio between the quantities of the two alcohols used. In certain situations, where a mixture of alcohols having similar molecular weights and structures can be procured at a lower cost than a pure alcohol compound, this embodiment can be highly economic to produce a mixture of ester compounds with similar molecular structures, molecular weights, and properties suitable as a lubricating oil base stock product.

In the gamma-branched alcohol having a formula (F-IV), preferably $R^1$ and $R^2$ are independently linear alkyl groups such as: ethyl, n-propyl, n-butyl, n-pentyl, n-hexyl, n-heptyl, n-octyl, n-nonyl, n-decyl, n-undecyl, n-dodecyl, n-tridecyl, n-tetradecyl, n-pentadecyl, n-hexadecyl, n-heptadecyl, n-octadecyl, n-nonadecyl, n-icosyl, n-henicosyl, n-docosyl, n-tricosyl, n-tetracosyl, n-pentacosyl, n-hexacosyl, n-octacosyl, and n-triacontyl. Preferably the total number of carbon atoms in linear $R^1$ and/or $R^2$ is an even number. Preferably the total number of carbon atoms in linear $R^1$ and $R^2$ combined is from a1 to a2, where a1 and a2 can be, independently, 8, 10, 12, 14, 16, 18, 20, 22, 24, 26, 28, 30, 32, 34, 36, 38, 40, 42, 44, 46, 48, as long as a1<a2. Preferably the total number of carbon atoms in linear $R^1$ and $R^2$ combined is from 8 to 48, more preferably from 8 to 40, still more preferably from 8 to 32, still more preferably from 8 to 28, still more preferably from 8 to 26, still more preferably from 8 to 24, still more preferably from 8 to 22, and still more preferably from 8 to 20.

In the gamma-branched alcohol having a formula (F-IV), preferably the total number of carbon atoms in linear $R^1$ and $R^2$ combined is from b1 to b2, where b1 and b2 can be, independently, 8, 10, 12, 14, 16, 18, 20, 22, 24, 26, 28, 30, 32, 34, 36, 38, 40, 42, 44, 46, 48, as long as b1<b2.

Preferably the total number of carbon atoms in $R^1$ and $R^2$ combined is in a range from 8 to 48, more preferably from 8 to 40, still more preferably from 8 to 32, still more preferably from 8 to 28, still more preferably from 8 to 26, still more preferably from 8 to 24, still more preferably from 8 to 22, and still more preferably from 8 to 20.

In the gamma-branched alcohol having a formula (F-IV), preferably the difference in carbon numbers contained $R^1$ and $R^2$ is two (2). In such case, it is particularly preferred that both $R^1$ and $R^2$ contain even number of carbon atoms. Thus, one of $R^1$ and $R^2$ preferably contains 4, 6, 8, 10, 12, 14, 16, 18, 20, 22, 24, 26, or 28 carbon atoms, and the other contains two more carbon atoms. Still more preferably, one of $R^1$ and $R^2$ preferably comprises 6, 8, 10, 12, 14, 16, 18, 20, or 22 carbon atoms, and the other comprises two more carbon atoms. In these embodiments, preferably both $R^1$ and $R^2$ are linear alkyl groups. A class of such gamma-branched alcohols where both $R^1$ and $R^2$ are linear alkyl groups can be advantageously made by reduction (e.g., hydrogenation) of its corresponding aldehyde, which, in term, can be produced from hydroformylation of its corresponding olefin, which in turn, can be produced from the dimerization of an alpha-olefin as illustrated in the following reaction Scheme-I, where $R^g$ can be any alkyl group, preferably a linear alkyl group, still more preferably a linear alkyl group having even number of carbon atoms:

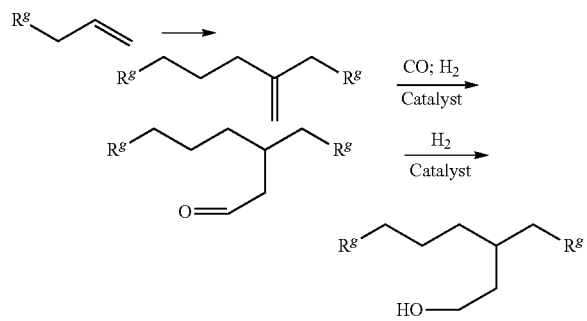

Scheme-I.

Dimerization of the olefin $R^g$—$CH_2$—$CH$=$CH_2$ in the first reaction shown above can be effected in the presence of a catalyst system such as one comprising a metallocene compound. Specific examples of Scheme-I is provided in Part A of the Examples provided in the present disclosure. As can be seen from Scheme-I, where Rg is a linear alkyl group, the final alcohol produced contains two linear alkyl groups ($R^g$—$CH_2$— and $R^g$—$CH_2CH_2CH_2$—) connected to the gamma-carbon that differ in terms of number of carbon atoms contained therein by two (2). Many linear alpha-olefins represented by formula $R^g$—$CH_2$—$CH$=$CH_2$ are commercially available: 1-butene, 1-pentene, 1-hexene, 1-octene, 1-decene, 1-dodecene, 1-tetradecene, 1-hexadecene, 1-octadecene, and the like. They can be conveniently used to fabricate gamma-branched alcohol 3-ethylheptan-1-ol, 3-propyloctan-1-ol, 3-butylnonan-1-ol, 3-hexylundecan-1-ol, 3-octyltridecan-1-ol, 3-decylpentadecan-1-ol, 3-dodecylheptadecan-1-ol, 3-tetradecylnonadecan-1-ol, 3-hexadecylhenicocan-1-ol, and 3-octadecyltricosan-1-ol, respectively.

Preferred examples of gamma-branched alcohols useful in the process of the present disclosure include the following: 3-ethylheptan-1-ol; 3-propyloctan-1-ol, 3-butylnonan-1-ol; 3-hexylundecan-1-ol; 3-octyltridecan-1-ol; 3-decylpentadecan-1-ol; and 3-dodecylheptadecan-1-ol.

The catalyst used in the esterification reaction can be an acid, desirably a strong acid. Non-limiting examples of such acid are: p-toluenesulfonic acid monohydride (PTSA), titanium isopropoxide and sulfuric acid.

The reaction can be advantageously carried out in the presence of a solvent. The specific solvent used is not critical as long as it is inert in the reaction. Non-limiting examples of the solvent are the following and mixtures thereof: benzene, toluene, xylenes, ethylbenzene, n-pentane and isomers thereof, n-hexane and isomers thereof, n-heptane and isomers thereof, n-octane and isomers thereof, and cyclohexane and saturated isomers thereof. Preferred examples of solvents are the following and mixtures thereof: toluene, n-hexane and isomers thereof, cyclohexane and saturated isomers thereof, ethylbenzene, and any xylene and mixtures thereof.

The reaction mixture from the esterification reaction typically comprises the intended ester product(s), water, and one or more of unreacted acid/anhydride and alcohol, and byproducts such as ethers, and esters of the acid catalyst. Continuous removal of water from the reaction system can result in higher yield of the ester compounds. Components in the reaction mixture having a boiling point lower than the intended gamma-branched alcohol-derived ester can be removed by vacuum. Purification methods such as solvent extraction, chromatography, distillation, and the use of sorbents can be carried out to remove byproducts from reaction mixture to finally obtain one compound of formula (F-I), or a mixture of multiple compounds of formula (F-I), depending on the reactants used, which can be used as a base stock product, or combined with other, similar compounds to form a base stock product.

IV. Lubricating Oil Compositions Containing Gamma-Branched Alcohol-Derived Ester IV. 1 General The gamma-branched alcohol-derived ester base stocks of this disclosure are useful in formulating lubricating oils. The oil composition of the present disclosure summarized above can be a portion or the entirety of a lubricating oil formulation ready to be used in its intended application. Thus, the oil composition can be: (i) a mixture of the gamma-branched alcohol-derived ester base stock and the remainder of the formulation absent the gamma-branched alcohol-derived ester base stock; (ii) a mixture of the gamma-branched alcohol-derived ester base stock with one or more other base stocks contained in the lubricating oil formulation absent the additive components in the lubricating oil formulation; (iii) a mixture of the gamma-branched alcohol-derived ester base stock and all other base stocks contained in the lubricating oil formulation but absent any additive components that may be present in the lubricating oil formulation; (iv) a mixture of the gamma-branched alcohol-derived ester base stock and one or more other base stocks, but not all the other base stocks, contained in the lubricating oil formulation, and at least a portion of the additive components contained in the lubricating oil formulation; and (v) a mixture of the gamma-branched alcohol-derived ester base stock and all additive components contained in the lubricating oil formulation, but no other base stocks contained in the lubricating oil formulation.

Therefore, to make a final lubricating oil formulation as a product, one may add additional components, such as other base stocks, additional quantities of the materials already present in the oil composition, additive components, and the like, to the oil composition. A particularly preferred embodiment of the oil composition of the present disclosure; however, is a lubricating oil formulation.

The gamma-branched alcohol-derived ester base stock can be present in the lubricating oil formulation of this disclosure in an amount from about c1 to c2 wt %, based on the total weight of the oil composition, where c1 and c2 can be, independently, 1, 2, 3, 4, 5, 6, 7, 8, 9, 10, 15, 20, 25, 30, 35, 40, 45, 50, 55, 60, 65, 70, 75, 80, 85, 90, 95, or 99 as long as c1<c2. Preferably c1=3, and c2=95. More preferably c1=5, and c2=90. Still more preferably c1=5, and c2=80. Still more preferably c1=5, and c2=50. In general, it is desirable that the lubricating oil formulation contains the gamma-branched alcohol-derived ester base stock as a co-base stock. However, it is also contemplated that the lubricating oil formulation of this disclosure may contain the gamma-branched alcohol-derived ester base stock as a primary base stock, and in an extreme case, the lubricating oil formulation may consist essentially of a gamma-branched alcohol-derived ester base stock and additives.

Owing to the high polarity of the gamma-branched alcohol-derived ester base stocks resulting from the ester group in their molecular structures, the lubricating oil compositions of the present disclosure can have an improved polar additive and sludge solvency and dispersancy compared to other lubricating oil compositions free of ester-type base stocks. In addition, a lubricating oil formulation including a gamma-branched alcohol-derived ester base stock can have improved seal compatibility compared to formulations free of ester-type base stocks.

IV. 2 Other Base Stocks Useful in the Lubricating Oil

A wide range of lubricating oil base stocks known in the art can be used in conjunction with the gamma-branched alcohol-derived ester base stock in the lubricating oil formulations of the present disclosure, as a primary base stock or a co-base stock. Such other base stocks can be either derived from natural resources or synthetic, including un-refined, refined, or re-refined oils. Un-refined oil base stocks include shale oil obtained directly from retorting operations, petroleum oil obtained directly from primary distillation, and ester oil obtained directly from a natural source (such as plant matters and animal tissues) or directly from a chemical esterification process. Refined oil base stocks are those un-refined base stocks further subjected to one or more purification steps such as solvent extraction, secondary distillation, acid extraction, base extraction, filtration, and percolation to improve the at least one lubricating oil property. Re-refined oil base stocks are obtained by processes analogous to refined oils but using an oil that has been previously used as a feed stock.

API Groups I, II, III, R$^1$ and V are broad categories of base stocks developed and defined by the American Petroleum Institute (API Publication 1509; www.API.org) to create guidelines for lubricating oil base stocks. Group I base stocks generally have a viscosity index of from about 80 to 120 and contain greater than about 0.03% sulfur and less than about 90% saturates. Group II base stocks generally have a viscosity index of from about 80 to 120, and contain less than or equal to about 0.03% sulfur and greater than or equal to about 90% saturates. Group III base stocks generally have a viscosity index greater than about 120 and contains less than or equal to about 0.03% sulfur and greater than about 90% saturates. Group R$^1$ includes polyalphaolefins (PAO). Group V base stocks include base stocks not included in Groups I-IV. The table below summarizes properties of each of these five groups.

| Base Stock Properties | | | |
|---|---|---|---|
| | Saturates | Sulfur | Viscosity Index |
| Group I | Higher than 90 and/or | Higher than 0.03% and | At least 80 and at most 120 |
| Group II | Higher than 90 and | At most 0.03% and | At least 80 and at most 120 |
| Group III | At least 90 and | At most 0.03% and | At least 120 |
| Group IV | | PAO products | |
| Group V | All other products not included in Groups I, II, III, and IV | | |

Natural oils include animal oils (e.g. lard), vegetable oils (e.g., castor oil), and mineral oils. Animal and vegetable oils possessing favorable thermal oxidative stability can be used. Of the natural oils, mineral oils are preferred. Mineral oils vary widely as to their crude source, e.g., as to whether they are paraffinic, naphthenic, or mixed paraffinic-naphthenic. Oils derived from coal or shale are also useful in the present disclosure. Natural oils vary also as to the method used for their production and purification, e.g., their distillation range and whether they are straight run or cracked, hydrorefined, or solvent extracted.

Group II and/or Group III base stocks are generally hydroprocessed or hydrocracked base stocks derived from crude oil refining processes.

Synthetic base stocks include polymerized and interpolymerized olefins (e.g., polybutylenes, polypropylenes, propylene isobutylene copolymers, ethylene-olefin copolymers, and ethylene-alphaolefin copolymers).

Synthetic polyalphaolefins ("PAO") base stocks are placed into Group IV. Advantageous Group IV base stocks are those made from one or more of C6, C8, C10, C12, and C14 linear alpha-olefins ("LAO"s). These base stocks can be commercially available at a wide range of viscosity, such as a KV100 in the range from 1.0 to 1,000 cSt. The PAO base stocks can be made by polymerization of the LAO(s) in the presence of Lewis-acid type catalyst or a metallocene compound-based catalyst system. High quality Group IV PAO commercial base stocks include the SpectraSyn™ and SpectraSyn Elite™ series available from ExxonMobil Chemical Company having an address at 4500 Bayway Drive, Baytown, Tex. 77520, United States.

All other synthetic base stocks, including but not limited to alkyl aromatics and synthetic esters are in Group V.

Additional esters not in the gamma-branched alcohol-derived ester category in a minor amount may be useful in the lubricating oil formulations of this disclosure. Additive solvency and seal compatibility characteristics may be imparted by the use of esters such as the esters of dibasic acids with monoalkanols and the polyol esters of monocarboxylic acids. Esters of the former type include, e.g., the esters of dicarboxylic acids such as phthalic acid, succinic acid, sebacic acid, fumaric acid, adipic acid, linoleic acid dimer, malonic acid, alkyl malonic acid, alkenyl malonic acid, etc., with a variety of alcohols such as butyl alcohol, hexyl alcohol, dodecyl alcohol, 2-ethylhexyl alcohol, etc. Specific examples of these types of esters include dibutyl adipate, di(2-ethylhexyl) sebacate, di-n-hexyl fumarate, dioctyl sebacate, diisooctyl azelate, diisodecyl azelate, dioctyl phthalate, didecyl phthalate, dieicosyl sebacate, etc. Useful ester-type Group V base stock include the Esterex™ series commercially available from ExxonMobil Chemical Company.

One or more of the following may be used as a base stock in the lubricating oil of the present disclosure as well: (1)

one or more Gas-to-Liquids (GTL) materials; and (2) hydrodewaxed, hydroisomerized, solvent dewaxed, or catalytically dewaxed base stocks derived from synthetic wax, natural wax, waxy feeds, slack waxes, gas oils, waxy fuels, hydrocracker bottoms, waxy raffinate, hydrocrackate, thermal crackates, foots oil, and waxy materials derived from coal liquefaction or shale oil. Such waxy feeds can be derived from mineral oils or non-mineral oil processing or can be synthetic (e.g., Fischer-Tropsch feed stocks). Such base stocks preferably comprise linear or branched hydrocarbyl compounds of C20 or higher, more preferably C30 or higher.

The lubricating oil formulations of the present disclosure can comprise one or more Group I, II, III, IV, or V base stocks in addition to the gamma-branched alcohol-derived ester base stock. Preferably, Group I base stocks, if any, are present at a relatively low concentration if a high quality lubricating oil is desired. Group I base stocks may be introduced as a diluent of an additive package at a small quantity. Groups II and III base stocks can be included in the lubricating oil formulations of the present disclosure, but preferably only those with high quality, e.g., those having a VI from 100 to 120. Group IV and V base stocks, preferably those of high quality, are desirably included into the lubricating oil formulations of the present disclosure.

IV. 3 Lubricating Oil Additives

The formulated lubricating oil useful in the present disclosure may additionally contain one or more of the commonly used lubricating oil performance additives including but not limited to dispersants, detergents, viscosity modifiers, antiwear additives, corrosion inhibitors, rust inhibitors, metal deactivators, extreme pressure additives, anti-seizure agents, wax modifiers, viscosity modifiers, fluid-loss additives, seal compatibility agents, lubricity agents, anti-staining agents, chromophoric agents, defoamants, demulsifiers, densifiers, wetting agents, gelling agents, tackiness agents, colorants, and others. For a review of many commonly used additives and the quantities used, see: (i) Klamann in Lubricants and Related Products, Verlag Chemie, Deerfield Beach, Fla.; ISBN 0-89573-177-0; (ii) "Lubricant Additives," M. W. Ranney, published by Noyes Data Corporation of Parkridge, N.J. (1973); (iii) "Synthetics, Mineral Oils, and Bio-Based Lubricants," Edited by L. R. Rudnick, CRC Taylor and Francis, 2006, ISBN 1-57444-723-8; (iv) "Lubrication Fundamentals," J. G. Wills, Marcel Dekker Inc., (New York, 1980); (v) Synthetic Lubricants and High-Performance Functional Fluids, 2nd Ed., Rudnick and Shubkin, Marcel Dekker Inc., (New York, 1999); and (vi) "Polyalphaolefins," L. R. Rudnick, Chemical Industries (Boca Raton, Fla., United States) (2006), 111 (Synthetics, Mineral Oils, and Bio-Based Lubricants), 3-36. Reference is also made to: (a) U.S. Pat. No. 7,704,930 B2; (b) U.S. Pat. No. 9,458,403 B2, Column 18, line 46 to Colum 39, line 68; (c) U.S. Pat. No. 9,422,497 B2, Column 34, line 4 to Colum 40, line 55; and (d) U.S. Pat. No. 8,048,833 B2, Column 17, line 48 to Colum 27, line 12, the disclosures of which are incorporated herein in their entirety. These additives are commonly delivered with varying amounts of diluent oil that may range from 5 wt % to 50 wt % based on the total weight of the additive package before incorporation into the formulated oil. The additives useful in this disclosure do not have to be soluble in the lubricating oil formulations. Insoluble additives in oil can be dispersed in the lubricating oil formulations of this disclosure.

When lubricating oil formulations contain one or more of the additives discussed above, the additive(s) are blended into the oil composition in an amount sufficient for it to perform its intended function.

It is noted that many of the additives are shipped from the additive manufacturer as a concentrate, containing one or more additives together, with a certain amount of base oil diluents.

Examples of techniques that can be employed to characterize the gamma-branched alcohol-derived ester base stock described above include, but are not limited to, analytical gas chromatography, nuclear magnetic resonance, thermogravimetric analysis (TGA), inductively coupled plasma mass spectrometry, differential scanning calorimetry (DSC), and volatility and viscosity measurements.

The present invention is further illustrated by the following non-limiting examples.

EXAMPLES

In the following examples, kinematic viscosity at 100° C. ("KV100") and 40° C. ("KV40") of fluids were determined pursuant to ASTM standards D-445; viscosity index ("VI") was determined pursuant to ASTM standard D-2270; and Noack volatility ("NV") were determined using thermal gravimetric analysis ("TGA").

Part A: Synthesis of 3-Octyltridecan-1-Ol

A1. Synthesis of 9-Methylenenonadecane

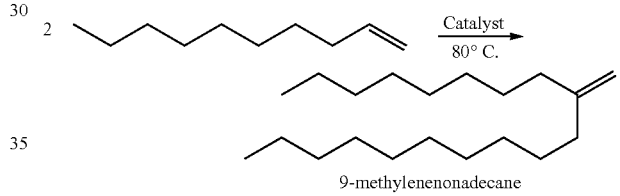

9-methylenenonadecane

Into a batch reactor was charged 5000 grams of 1-decene (98.6% decene, 0.7% octene, 0.7% dodecene), into which 50 grams of 10% MAO solution was added and held for 60 minutes at 80° C. 450 grams of catalyst solution (1.4 wt % biscyclopentadienyl zirconium (IV) dichloride dissolved in toluene) was subsequently added over 52 minutes. The reactor was held at 80° C. for 6 hours before the reaction was cooled and quenched with 10 mL of water. Gas chromatography showed reactor conversion was 74% with 88% selectivity to dimer and 12% selectivity to trimer and heavier species.

Filter aid was added thereafter into the fluid, which was filtered to remove Zr and/or Al-containing solid particles. The resultant mixture was then flashed to remove the residual monomer and heavies product to isolate the dimer species. The recovered dimer product was measured to contain dimers of the starting olefin at a concentration of 99.5 wt % by GC and a concentration of 9-methylenenonadecane at 98 mol % (by $^1$H NMR).

A2. Synthesis of 3-Octyltridecan-1-Ol

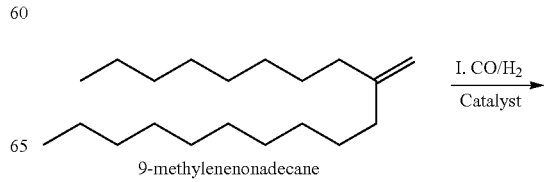

9-methylenenonadecane

-continued

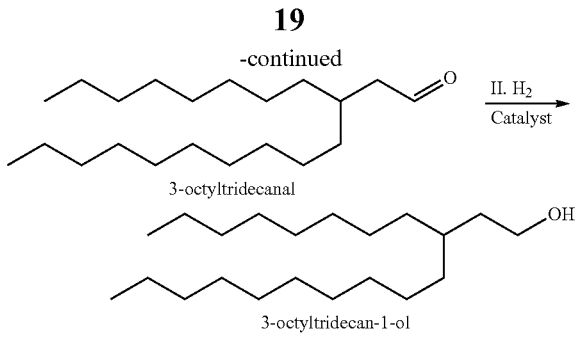

A2-I: Hydroformylation of 9-Methylenenonadecane

Into a 1-gallon autoclave equipped with mechanical stirrer, 3.24 grams of (acetylacetonato)dicarbonylrhodium and 4.87 grams of triphenyl phosphine (together ("Catalyst")) was mixed with 2000 grams of the 9-methylenenonadecane-containing dimer product made in Step A1 above to form a slurry. The reaction was nitrogen purged and then purged with syngas (1:1 molar ratio $H_2$:CO). The autoclave was pressurized by syngas to 510 psig (3516 kPa, gauge pressure) at 26° C., where agitation begun. Under agitation and constant pressure, temperature was then raised from 26° C. to 100° C. Syngas pressure inside the autoclave was then raised to 700 psig (4826 kPa, gauge pressure) at this temperature and held under constant pressure and temperature for 18 hours before it was depressurized. The reaction product mixture, a dark liquid, was then discharged and filtered to remove solid particles and obtain a carbonyl product mixture. Olefin conversion in this step was measured to be 92.1% with selectivity to C21 carbonyl product estimated at 99%. Infrared absorption spectra of the carbonyl product mixture with an overlay of that of the 9-methylenenonadecane-containing dimer product made in Step A1 showed the formation of a peak at 1729.83 cm-1, indicating the formation of an aldehyde.

A2-II: Hydrogenation of the Carbonyl Product Mixture

Into a 1-gallon autoclave equipped with mechanical stirrer, the carbonyl product mixture made in A2-I above and 27.5 grams of Pt/C catalyst were charged to make a slurry. The autoclave was first purged three times with nitrogen. Next, the autoclave was pressured up with 100% $H_2$ to 500 psig (3447 kPa, gauge pressure) by $H_2$ and the temperature increased to 50° C. The pressure and temperature were then slowly ramped to 100° C. and 1500 psig (10,342 kPa, gauge pressure) over 2 hours. Then, the pressure and temperature was finally increased to 150° C. and 2250 psig (15,513 kPa, gauge pressure) over one hour. The reactor was held at these conditions for 72 hours and then depressurized. The resultant slurry was filtered by vacuum filtration to obtain a crude alcohol mixture. Extent of hydrogenation was measured to be 97.9% with a yield of heavy fractions (fractions having normal boiling points higher than that of 3-octyltridecan-1-ol) at 8.8%.

A2-III: Distillation to Obtain High-Purity 3-Octyltridecan-1-Ol

The crude alcohol mixture produced from A2-II above was distilled to remove light fractions (fractions having normal boiling points lower than that of 3-octyltridecan-1-ol, such as 9-methylnonadecane) and undesired heavy fractions from the hydrogenated alcohol product to produce a high-purity fraction of 3-octyltridecan-1-ol (the "C21-alcohol"). The C21-alcohol purity was measured to be 98.2 wt %, with the balance being predominantly 9-methylnonadecane resulting from the hydrogenation in step A2-II of the residual 9-methylenenonadecane from step A2-I. $^{13}C$ NMR of the C21-alcohol, included in FIG. 1, shows the alcohol is pure 3-octyltridecan-1-ol.

The C21-alcohol was measured to have the following properties: a KV100 of 4.18 cSt, a KV40 of 31.4 cSt, a viscosity index of −60.4, a flash point determined pursuant to ASTM D93 of 193° C., a density determined pursuant to ASTM D-4052 of 0.84 gram·cm$^{-3}$, and a refractive index determined pursuant to ASTM D-1218 of 1.453.

Part B: Synthesis of Various Esters of 3-Octyltridecan-1-Ol

Example B1: Synthesis of 3-Octyltridecyl Acetate

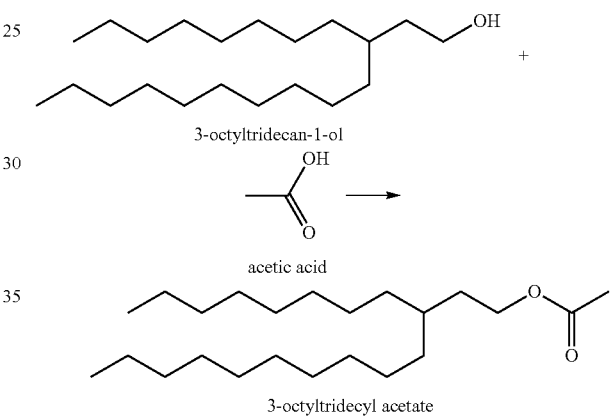

Into a 250 ml glass reactor fitted with an Argon purge was placed the acetic acid (23.5 grams, 0.39 moles), 3-octyltridecan-1-ol (40.6 grams, 0.13 moles) made in Example 1 above (the high-purity 3-octyltridecan-1-ol from step A2-III) and p-toluene sulfonic acid monohydrate (24.7 grams, 0.13 moles). The mixture above was purged with Argon at room temperature for one hour. The mixture was then heated to 100° C. under Argon purge for 18 hours. The mixture was then cooled to room temperature. The residue was then dissolved into 100 ml with ethyl acetate and placed into a separatory funnel. The ethyl acetate solution was extracted once with 100 ml of distilled water. The ethyl acetate layer was washed with 250 ml 10 wt % $NaHCO_3$ aqueous solution followed by 250 ml saturated NaCl aqueous solution. The ethyl acetate solution was dried over $MgSO_4$ and then filtered. The ethyl acetate was removed on the rotary evaporator from the solution. The residue from the rotary evaporator was placed on a Kugelrohr vacuum distillation apparatus where the ester was distilled. Weight of distilled product was 34.57 grams (75%). The isolated product was characterized by $^1HNMR$ and $^{13}CNMR$. $^1H$ NMR (CDCl$_3$): δ3.96 (d, 2H, O—CH$_2$—), 2.04 (S, 3H, O=C—CH$_3$), 1.62–1.26 (m, 35H, —CH$_2$—), 0.88 (t, 6H, CH$_3$). $^{13}C$ NMR (CDCl$_3$): 61.07, 37.22, 36.87, 34.32, 33.72, 32.83, 31.91, 30.15, 30.04, 29.73, 29.67, 29.38, 27.09, 26.56, 22.69, 19.67, 14.07.

Example B2: Synthesis of 3-Octyltridecyl Pentanoate

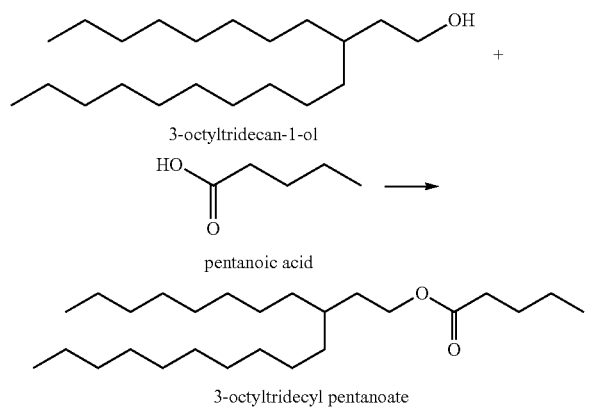

3-octyltridecan-1-ol pentanoic acid 3-octyltridecyl pentanoate

Into a 250 ml glass reactor fitted with an Argon purge was placed the pentanoic acid (20.5 grams, 0.2 moles), 3-octyltridecan-1-ol (30 grams, 0.1 moles) made in Example 1 above (the high-purity 3-octyltridecan-1-ol from step A2-III) and p-toluene sulfonic acid monohydrate (PTSA) (19 grams, 0.1 moles). The mixture above was purged with Argon at room temperature for one hour. The mixture was then heated to 100° C. under Argon purge for 18 hours. The mixture was then cooled to room temperature. The residue was then dissolved into 100 ml with ethyl acetate and placed into a separatory funnel. The ethyl acetate solution was extracted once with 100 ml of distilled water. The ethyl acetate layer was washed with 250 ml 10 wt % NaHCO3 aqueous solution followed by 250 ml saturated NaCl aqueous solution. The ethyl acetate solution was dried over MgSO4 and then filtered. The ethyl acetate was removed on the rotary evaporator from the solution. The residue from the rotary evaporator was placed on a Kugelrohr vacuum distillation apparatus where the ester was distilled. Weight of distilled product was 29.7 grams (75%). $^1$H NMR (CDCl$_3$): δ4.10 (t, 2H, O—CH$_2$—), 2.27 (7, 2H, O=C—CH$_3$), 1.62-1.26 (m, 39H, —CH$_2$—), 0.87 (t, 9H, CH$_3$). $^{13}$C NMR (CDCl$_3$): 171.81, 62.82, 34.56, 34.10, 33.75, 33.58, 32.45, 31.91, 31.28, 30.01, 29.69, 29.68, 29.64, 29.63, 29.35, 27.08, 26.69, 26.53, 22.84, 22.67, 22.27. IR (cm$^{-1}$): 2956, 2924, 2854, 1739, 1466, 1378, 1244, 1171, 1098, 721.

Example B3: Synthesis of 3-Octyltridecyl Hexanoate

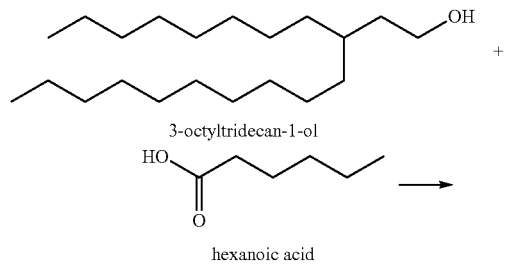

3-octyltridecan-1-ol hexanoic acid

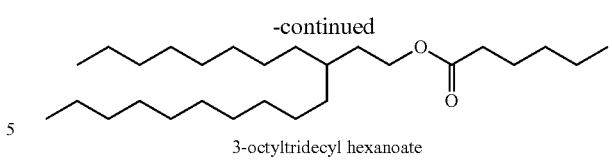

3-octyltridecyl hexanoate

Into a 250 ml glass reactor fitted with an Argon purge was placed the hexanoic acid (23.2 grams, 0.2 moles), 3-octyltridecan-1-ol (30 grams, 0.1 moles) and p-toluene sulfonic acid monohydrate (19 grams, 0.1 moles). The mixture above was purged with Argon at room temperature for one hour. The mixture was then heated to 100° C. under Argon purge for 18 hours. The mixture was then cooled to room temperature. The residue was then dissolved into 100 ml with ethyl acetate and placed into a separatory funnel. The ethyl acetate solution was extracted once with 100 ml of distilled water. The ethyl acetate layer was washed with 250 ml 10 wt % NaHCO$_3$ aqueous solution followed by 250 ml saturated NaCl aqueous solution. The ethyl acetate solution was dried over MgSO$_4$ and then filtered. The ethyl acetate was removed on the rotary evaporator from the solution. The residue from the rotary evaporator was placed on a Kugelrohr vacuum distillation apparatus where the ester was distilled. Weight of distilled product was 30.79 grams (74%). The isolated product was characterized by $^1$HNMR. $^1$HNMR (CDCl$_3$): δ4.10 (t, 2H, O—CH$_2$—), 2.27 (7, 2H, O=C—CH$_3$), 1.62-1.26 (m, 41H, —CH$_2$—), 0.87 (t, 9H, CH$_3$). $^{13}$C NMR (CDCl$_{13}$): 173.82, 62.74, 34.62, 34.41, 33.64, 32.47, 31.93, 31.35, 30.07, 29.72, 29.37, 26.53, 24.17, 22.27, 22.34, 14.06, 13.89. IR (cm$^{-1}$): 2956, 2924, 2854, 1739, 1466, 1378, 1244, 1171, 1098, 721.

Example B4: Synthesis of 3-Octyltridecyl Octanoate

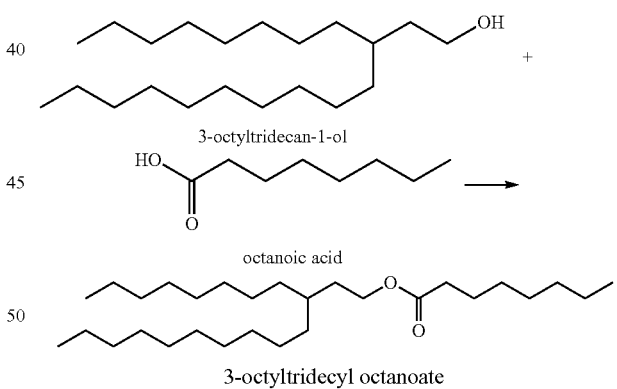

3-octyltridecan-1-ol octanoic acid 3-octyltridecyl octanoate

Into a 250 ml glass reactor fitted with an Argon purge was placed the octanoic acid (28.4 grams, 0.2 moles), 3-octyltridecan-1-ol (30 grams, 0.1 moles) and p-toluene sulfonic acid monohydrate (PTSA) (19 grams, 0.1 moles). The mixture above was purged with Argon at room temperature for one hour. The mixture was then heated to 100° C. under Argon purge for 18 hours. The mixture was then cooled to room temperature. The residue was then dissolved into 100 ml with ethyl acetate and placed into a separatory funnel. The ethyl acetate solution was extracted once with 100 ml of distilled water. The ethyl acetate layer was washed with 250 ml 10% NaHCO$_3$ aqueous solution followed by 250 ml saturated NaCl aqueous solution. The ethyl acetate solution was dried over MgSO$_4$ and then filtered. The ethyl acetate was removed on the rotary evaporator from the solution. The residue from the rotary evaporator was placed on a Kugelrohr vacuum distillation apparatus where the ester was distilled. Weight of distilled product was 32.85 grams (75%). $^1$H NMR (CDCl$_3$): δ3.96 (d, 2H, O—CH$_2$—), 2.31 (t, 2H, O=C—CH$_3$), 1.61 (m, 3H, —CH—, CH$_2$) 1.31 (m, 42H, —CH$_2$—), 0.87 (t, 9H, CH$_3$). $^{13}$C NMR (CDCl$_3$): 173.90, 62.84, 34.57, 34.43, 33.58, 32.45, 31.92, 31.68, 29.70, 29.69, 29.66, 29.37, 29.14, 26.54, 25.02, 22.69, 22.60, 14.09. IR (cm$^{-1}$): 29.56, 2924, 2854, 1738, 1466, 1377, 1167, 1104, 722.

Example B5: Synthesis of 3-Octyltridecyl 3-Phenylpropanoate

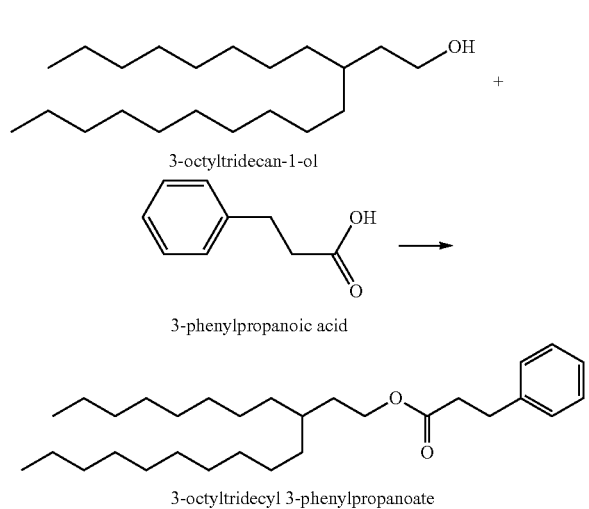

Into a 250 ml glass reactor fitted with an Argon purge was placed the 3-phenylpropionic acid (18.0 grams, 0.12 moles), 3-octyltridecan-1-ol (30 grams, 0.1 moles) made in Example 1 above (the high-purity 3-octyltridecan-1-ol from step A2-III) and p-toluene sulfonic acid monohydrate (PTSA) (19 grams, 0.1 moles). The mixture above was purged with Argon at room temperature for one hour. The mixture was then heated to 100° C. under Argon purge for 18 hours. The mixture was then cooled to room temperature. The residue was then dissolved into 100 ml with ethyl acetate and placed into a separating funnel. The ethyl acetate solution was extracted once with 100 ml of distilled water. The ethyl acetate layer was washed with 250 ml 10 wt % NaHCO$_3$ aqueous solution followed by 250 ml saturated NaCl aqueous solution. The ethyl acetate solution was dried over MgSO$_4$ and then filtered. The ethyl acetate was removed on a rotary evaporator. The residue from the rotary evaporator was placed on a Kugelrohr vacuum distillation apparatus where the ester was distilled and purified. The isolated product was characterized by $^1$HNMR and IR. $^1$H NMR (CDCl$_3$): δ6.37 (m, 4H, Ph), 3.23 (t, 2H, O=C—CH$_2$—), 2.10 (t, 2H, —CH$_2$—), 1.76 (t, 2H, —CH$_2$—), 1.53–1.25 (m, 37H) 0.86 (t, 6H, CH$_3$). $^{13}$C NMR: 172.87, 140.44, 128.35, 128.15, 126.12, 63.06, 35.90, 34.50, 33.42, 32.26, 31.17, 30.94, 29.92, 29.56, 29.20, 26.39, 22.58, 13.95. IR (cm$^{-1}$): 3064, 3028, 2955, 2924, 2853, 1737, 1605, 1497, 1454, 1377, 1290, 1161, 1077, 749, 721, 697.

Example B6: Synthesis of 3-Octyltridecyl Benzoate

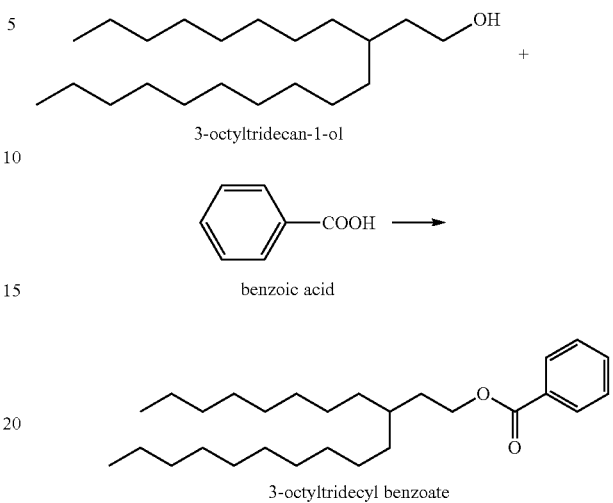

Into a 250 ml glass reactor fitted with an Argon purge was placed the benzoic acid (14.6 grams, 0.12 moles), 3-octyltridecan-1-ol (30 grams, 0.1 moles) made in Example 1 above (the high-purity 3-octyltridecan-1-ol from step A2-III) and p-toluene sulfonic acid monohydrate (19 grams, 0.1 moles). The mixture above was purged with Argon at room temperature for one hour. The mixture was then heated to 100° C. under Argon purge for 18 hours. The mixture was then cooled to room temperature. The residue was then dissolved into 100 ml with ethyl acetate and placed into a separating funnel. The ethyl acetate solution was extracted once with 100 ml of distilled water. The ethyl acetate layer was washed with 250 ml 10 wt % NaHCO$_3$ aqueous solution followed by 250 ml saturated NaCl aqueous solution. The ethyl acetate solution was dried over MgSO$_4$ and then filtered. The ethyl acetate was removed on the rotary evaporator from the solution. The residue from the rotary evaporator was placed on a Kugelrohr vacuum distillation apparatus where the ester was distilled. The isolated product was characterized by $^1$HNMR and IR. $^1$H NMR (CDCl$_3$): δ8.03–7.41 (m, 4H, Ph), 4.35 (t, 2H, O=C—CH$_2$—), 1.72 (q, 2H, —CH$_2$—), 1.53–1.25 (m, 34H) 0.86 (t, 6H, CH$_3$). $^{13}$C NMR: 166.72, 132.76, 130.57, 129.55, 128.30, 63.68, 34.74, 33.68, 32.50, 31.93, 30.08, 29.75, 29.38, 26.63, 22.68, 14.13. IR (cm$^{-1}$): 2955, 2924 2853, 1723, 1602, 1585, 1451, 1377, 1314, 1272, 1175, 1112, 1069, 1026, 709, 686, 676.

Part C: Comparative Examples C1-C6

A Low-Viscosity PAO Base Stock and Multiple Esters of 2-Octyl-1-Dodecanol

Example C1: Polyalphaolefin (PAO) SpectraSyn Plus™ 3.6

Polyalphaolefin (PAO) SpectraSyn Plus™ 3.6 is a Group IV base stock available commercially from ExxonMobil Chemical Company having an office at 4500 Bayway Drive, Baytown, Tex. 77520, United States of America.

Example C2: Synthesis of 2-Octyldodecyl Hexanoate

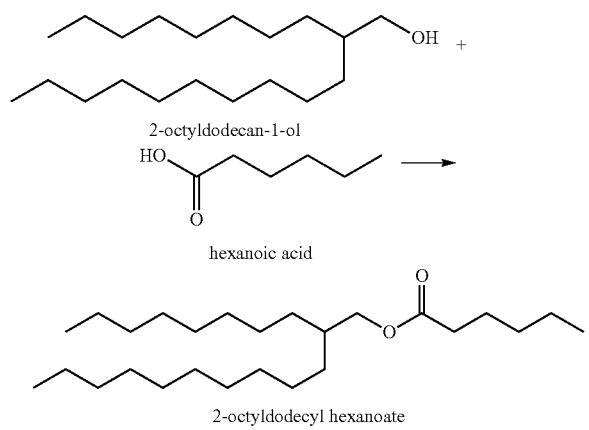

2-octyldodecan-1-ol hexanoic acid 2-octyldodecyl hexanoate

Into a 250 ml glass reactor fitted with an Argon purge was placed the hexanoic acid (23.2 grams, 0.2 moles), 2-octyl-1-dodecanol (29.9 grams, 0.1 moles) (Aldrich 97%) (the "C20-alcohol", which is a Guerbet alcohol) and p-toluene sulfonic acid monohydrate (19 grams, 0.1 mole). The mixture above was purged with Argon at room temperature for one hour. The mixture was then heated to 100° C. under Argon purge for 18 hours. The mixture was then cooled to room temperature. The residue was then dissolved into 100 ml with ethyl acetate and placed into a separatory funnel. The ethyl acetate solution was extracted once with 100 ml of distilled water. The ethyl acetate layer was washed with 250 ml 10 wt % NaHCO$_3$ aqueous solution followed by 250 ml saturated NaCl aqueous solution. The ethyl acetate solution was dried over MgSO$_4$ and then filtered. The ethyl acetate was removed on the rotary evaporator from the solution. The residue from the rotary evaporator was placed on a Kugelrohr vacuum distillation apparatus where the ester was distilled. $^1$H NMR (CDCl$_{13}$): δ3.96 (d, 2H, O—CH$_2$—), 2.31 (d, 2H, O=C—CH$_2$—), 1.61–1.26 (m, 39H, —CH$_2$—), 0.80 (t, 9H, CH$_3$). IR (cm$^{-1}$): 2955, 2925, 2854, 1733, 1466, 1378, 1234, 1168, 1102, 722.

Example C3: Synthesis of 2-Octyldodecyl Heptanoate

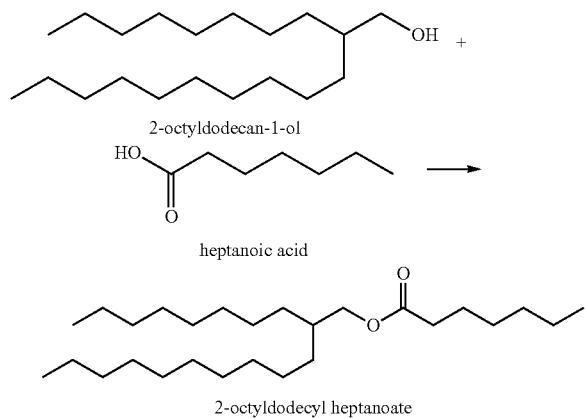

2-octyldodecan-1-ol heptanoic acid 2-octyldodecyl heptanoate

Into a 250 ml glass reactor fitted with an Argon purge was placed the heptanoic acid (26 grams, 0.2 moles), 2-octyl-1-dodecanol (29.9 grams, 0.1 moles) and p-toluene sulfonic acid monohydrate (19 grams, 0.1 moles). The mixture above was purged with Argon at room temperature for one hour. The mixture was then heated to 100° C. under Argon purge for 18 hours. The mixture was then cooled to room temperature. The residue was then dissolved into 100 ml with ethyl acetate and placed into a separatory funnel. The ethyl acetate solution was extracted once with 100 ml of distilled water. The ethyl acetate layer was washed with 250 ml 10% NaHCO$_3$ aqueous solution followed by 250 ml saturated NaCl aqueous solution. The ethyl acetate solution was dried over MgSO$_4$ and then filtered. The ethyl acetate was removed on the rotary evaporator from the solution. The residue from the rotary evaporator was placed on a Kugelrohr vacuum distillation apparatus where the ester was distilled. $^1$H NMR (CDCl$_{13}$): δ4.07 (d, 2H, O—CH$_2$—), 2.31 (d, 2H, O=C—CH$_2$—), 1.59–1.29 (m, 43H, —CH$_2$—), 0.88 (t, 9H, CH$_3$). IR (cm$^{-1}$): 2956, 2925, 2854, 1739, 1466, 1378, 1244, 1170, 1098, 721.

Example C4: Synthesis of 2-Octyldodecyl Nonanoate

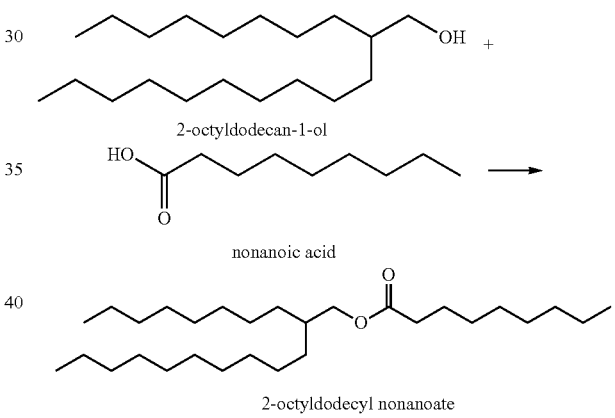

2-octyldodecan-1-ol nonanoic acid 2-octyldodecyl nonanoate

Into a 250 ml glass reactor fitted with an Argon purge was placed the nonanoic acid (20.5 grams, 0.2 moles), 2-octyl-1-dodecanol (29.9 grams, 0.1 moles) and p-toluene sulfonic acid monohydrate (19 grams, 0.1 moles). The mixture above was purged with Argon at room temperature for one hour. The mixture was then heated to 100° C. under Argon purge for 18 hours. The mixture was then cooled to room temperature. The residue was then dissolved into 100 ml with ethyl acetate and placed into a separatory funnel. The ethyl acetate solution was extracted once with 100 ml of distilled water. The ethyl acetate layer was washed with 250 ml 10 wt % NaHCO$_3$ aqueous solution followed by 250 ml saturated NaCl aqueous solution. The ethyl acetate solution was dried over MgSO$_4$ and then filtered. The ethyl acetate was removed on the rotary evaporator from the solution. The residue from the rotary evaporator was placed on a Kugelrohr vacuum distillation apparatus where the ester was distilled. $^1$H NMR (CDCl$_3$): δ4.01 (d, 2H, O—CH$_2$—), 2.31 (d, 2H, O=C—CH$_2$—), 1.63–1.33 (m, 45H, —CH$_2$—), 0.88 (t, 9H, CH$_3$). IR (cm$^{-1}$): 2955, 2954, 2854, 1738, 1466, 1378, 1251, 1251, 1165, 1107, 722.

Example C5: Synthesis of 2-Octyldodecyl Phenyl Propionate

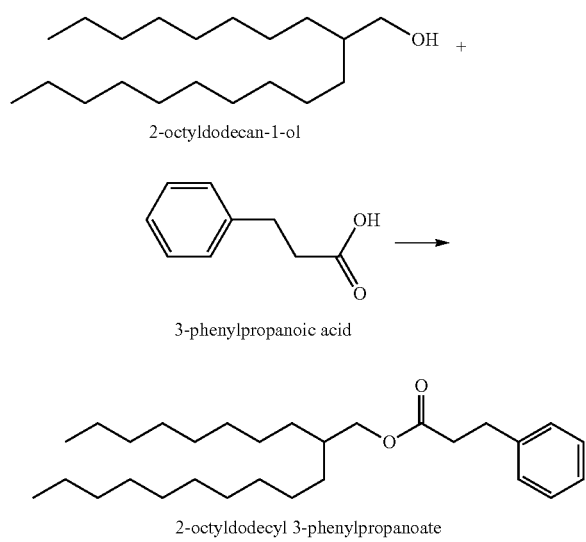

2-octyldodecan-1-ol 3-phenylpropanoic acid 2-octyldodecyl 3-phenylpropanoate

An ester of 2-octyldodecan-1-ol, 2-octyldodecyl phenylpropanoate, was made by using the method described in Example B5, with the exception that 3-octyltridecan-1-ol was replaced by 2-octyldodecan-1-ol.

Example C6: Synthesis of 2-Octyldodecyl Benzoate

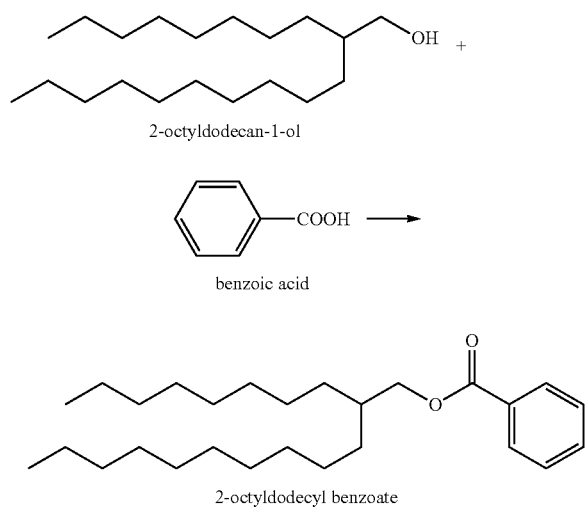

2-octyldodecan-1-ol benzoic acid 2-octyldodecyl benzoate

An ester of 2-octyldodecan-1-ol, 2-octyldodecyl benzoate, was made by using the method described in Example B6, with the exception that 3-octyltridecan-1-ol was replaced by 2-octyldodecan-1-ol.

Part D: Discussions of the Examples

D1. Lubricant Base Stock Properties

The ester fluids of inventive Examples B1, B2, B3, B4, B5, B6, comparative ester fluids of Examples C2, C3, C4, C5, and C6, and comparative Example C1, a commercial Group IV low-viscosity PAO base stock, were evaluated and results are shown below in TABLE I.

TABLE I

| Example No. | Fluid | Molecular Weight (g/mole) | KV100 (cSt) | KV40 (cSt) | Viscosity Index | Noack Volatility (TGA) (wt %) |
|---|---|---|---|---|---|---|
| B1 | C21-alcohol Acetate | 354.6 | 2.37 | 8.05 | 113 | 28.8 |
| B2 | C21-alcohol Pentanoate | 396.7 | 2.70 | 9.12 | 143 | 15.4 |
| B3 | C21-alcohol Hexanoate | 410.7 | 2.84 | 9.77 | 145 | 11.4 |
| B4 | C21-alcohol Octanoate | 438.8 | 3.18 | 11.5 | 151 | 7.9 |
| B5 | C21-alcohol Phenylpropionate | 444.7 | 3.64 | 14.4 | 142 | 4.4 |
| B6 | C21-alcohol Benzoate | 416.7 | 3.67 | 16.4 | 109 | 7.7 |
| C1 | PAO 3.6 | ~420.0 | 3.60 | 15.4 | 120 | 17.0 |
| C2 | C20-alcohol Hexanoate | 396.7 | 2.65 | 8.95 | 140 | 16.6 |
| C3 | C20-alcohol Heptanoate | 410.7 | 2.80 | 9.64 | 143 | 13.5 |
| C4 | C20-alcohol Nonanoate | 438.8 | 3.16 | 11.44 | 148 | 9.7 |
| C5 | C20-alcohol Phenylpropionate | 430.7 | 3.38 | 13.3 | 132 | 7.4 |
| C6 | C20-alcohol Benzoate | 402.7 | 3.51 | 15.7 | 101 | 9.5 |

To compare selective gamma-branched C21-alcohol based esters with selective beta-branched C20-alcohol (Guerbet alcohol) based esters, fluids of molecules having similar molecular weight were prepared in the above Examples B2-B6 and comparative Examples C2-C6. Structures of the esters are further provided in TABLE II below. As can be seen, esters of Examples B2 and C2 have the same molecular weight; so do esters of Examples B3 and C3; and esters of Examples B4 and C4. Esters of Examples B5 and B6 are slightly higher than those of the counterpart comparative Examples C5 and C6, by about 14 grams/mol, respectively.

TABLE II

| Inventive Example No. | Comparative Example No. |
|---|---|
| B2 — 3-octyltridecyl pentanoate | C2 — 2-octyldodecyl hexanoate |

TABLE II-continued

| Inventive Example No. | | Comparative Example No. | |
|---|---|---|---|
| B3 | 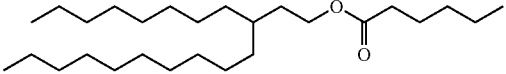 3-octyltridecyl hexanoate | C3 | 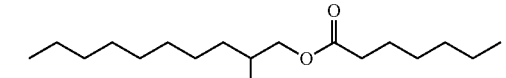 2-octyldodecyl heptanoate |
| B4 | 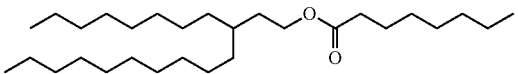 3-octyltridecyl octanoate | C4 | 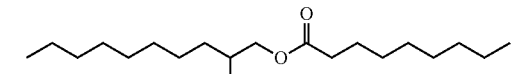 2-octyldodecyl nonanoate |
| B5 | 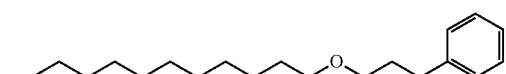 3-octyltridecyl 3-phenylpropanoate | C5 | 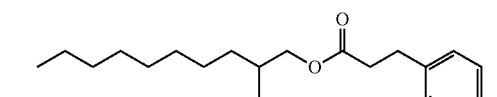 2-octyldodecyl 3-phenylpropanoate |
| B6 | 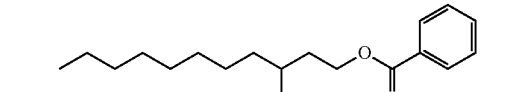 3-octyltridecyl benzoate | C6 | 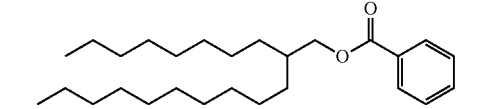 2-octyldodecyl benzoate |

Figure 2:
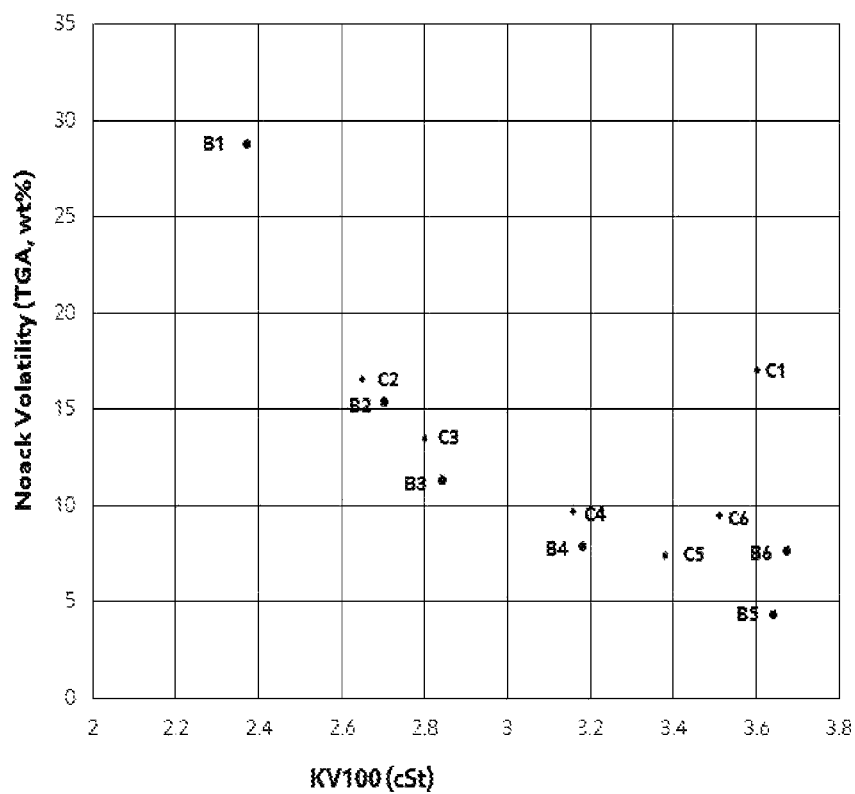
FIG. 2 is a diagram showing the KV100 and Noack volatility of a series of inventive examples and comparative examples in this disclosure.

The viscosity and volatility characteristics of ester fluids of Examples B1-B6, C2-C6 and PAO base stock Example C1 were plotted and results are shown in FIG. 2.

In general, for a fluid useful as a low-viscosity base stock having a KV100 in the range from 2.0 to 4.0 cSt, it is desirable to have a lower KV100 of the fluid, a lower Noack volatility, and a higher viscosity index, all other factors held equal, especially for the purpose of formulating an engine oil.

D2. Examples B2, B3, and B4 Vis-à-Vis Comparative Examples C2, C3, and C4

Figure 3:
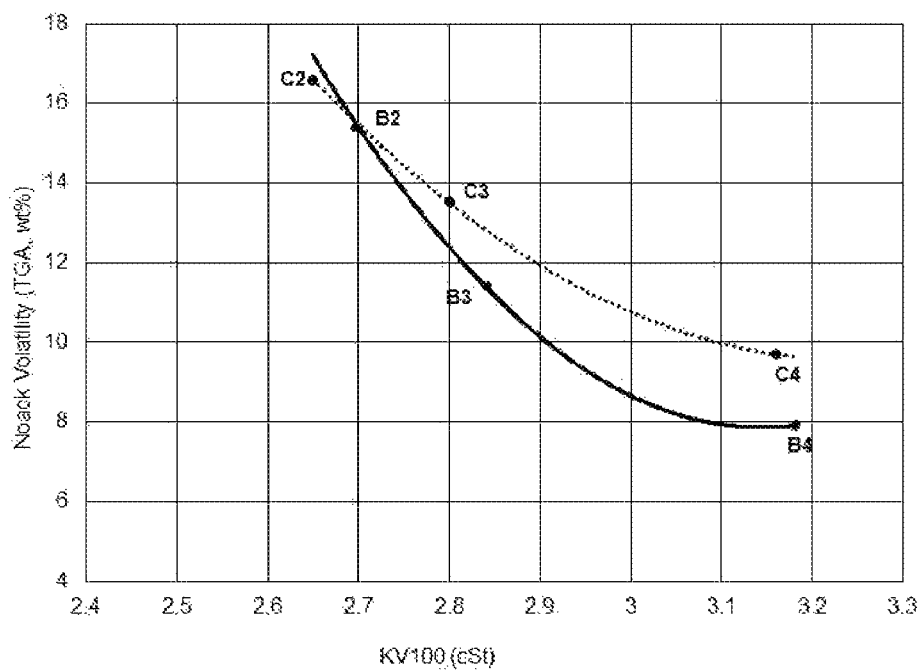
FIG. 3 is a diagram showing and comparing the KV100 and Noack volatility of inventive Examples B2, B3, and B4 and comparative Examples C2, C3, and C4.

FIG. 3 compares the KV100-Noack Volatility characteristics of selective gamma-branched C21-alcohols based esters (Example B2, B3, and B4) with selective beta-branched C20-alcohol esters (Example C2, C3, and C4).

The results show that directionally KV100-Noack Volatility performance of selective gamma-branched C21-alcohols based esters (Example B2, B3, and B4) is similar or better than selective beta-branched C20-alcohol (a Guerbet alcohol) based esters (Example C2, C3, and C4).

More specifically, the plotted data points for the C21-alcohols based esters (Example B2, B3, and B4) are well described by a second order polynomial expression $y=38.078x^2-239.52x+384.52$ with an $R^2$ value=1. It is expected that other (KV100, Noack Volatility) combinations defined by this expression, at least in the KV100 (x) range from x=2.65 to x=3.2, can be achieved with C21-alcohols based esters by modifying the carbon number of the linear acid or using blends of linear acids with a known average carbon number.

Additionally, the plotted data points for the C20-alcohol based esters (Example C2, C3, and C4) are well described by a second order polynomial expression $y=19.826x^2-128.72x+218.47$ with an $R^2$ value=1. It is expected that other (KV100, Noack Volatility) combinations defined by this expression, at least between the KV100 (x) range from x=2.65 to x=3.2, can be achieved with C20-alcohols based esters by modifying the carbon number of the linear acid or using blends of linear acids with a known average carbon number.

Moreover, both a C21-alcohol and C20-alcohol based ester could be prepared with a KV100 of 2.70 cSt and TGA Noack Volatility of 15.6%. However, for all ester base stock of this family with volatility below 15.6%, the C21-alcohol based ester will have lower volatility than a C20-alcohol based ester of equivalent viscosity. This is significant, as many personal vehicle engine oil standards required a Noack volatility of 15.0% or lower.

Moreover, for all ester base stocks of this family with volatility below 15.6%, the C21-alcohol based ester will have lower viscosity than a C20-alcohol based ester of equivalent volatility.

Figure 4:
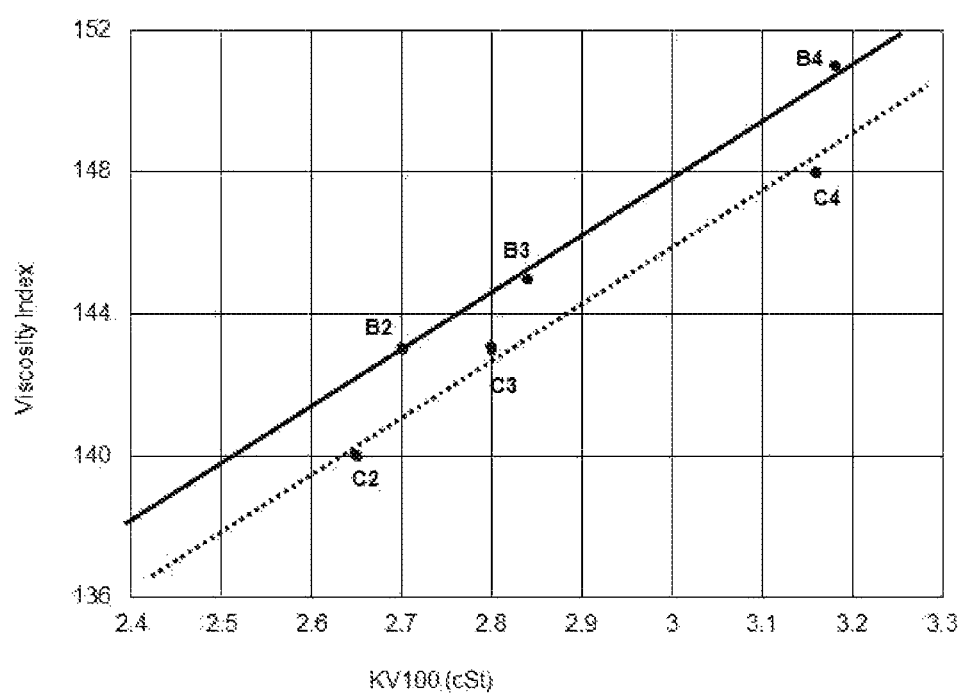
FIG. 4 is a diagram showing and comparing the KV100 and viscosity index of inventive Examples B2, B3, and B4 and comparative Examples C2, C3, and C4.

FIG. 4 compares the viscosity (KV100) and viscosity index characteristics of selective gamma-branched C21-alcohols based esters (Example B2, B3, and B4) with selective beta-branched C20-alcohol (a Guerbet alcohol) based esters (Example C2, C3, and C4).

The results show that directionally viscosity index of selective gamma-branched C21-alcohol based esters (Example B2, B3, and B4) is better than selective beta-branched C20-alcohol based esters (Example C2, C3, and C4) at the same molecular weight.

D3. Inventive Examples B5 and B6 Vis-à-Vis Comparative Examples C5 and C6

As can be seen from FIG. 2, inventive Example B5, a phenylpropanoate ester of a C21 gamma-branched alcohol, has higher viscosity index and lower Noack volatility than comparative Example C5, a corresponding phenylpropanoate ester of a C20 beta-substituted alcohol. Therefore, the base stock of Example B5 is superior to the base stock of Example C5.

As can be seen from FIG. 2, inventive Example B6, and benzoate ester of a C21 gamma-branched alcohol, has higher viscosity index and lower volatility than comparative Example C6, a corresponding benzoate ester of a C20 beta-substituted alcohol. Therefore, the base stock of Example B5 is superior to the base stock of Example C5.

It is noteworthy that the difference in the viscosity between the phenylpropanoate and benzoate esters of the gamma-branched C21-alcohol (i.e., differences in KV100 between inventive Examples B5 and B6, which is 0.03 and 2.00 cSt, respectively) is smaller than that the corresponding differences between the phenylpropanoate and benzoate esters of the C20 beta-substituted alcohol (i.e., differences in KV100 and KV40 between comparative Examples C5 and C6, which is 0.13 and 2.4 cSt, respectively). Without intending to be bound by a particular theory, it is believed that the difference may be due to higher flexibility of the molecule of the esters made from the gamma-branched alcohols. Thus, for base stocks of esters comprising a phenyl group, a carbonyl group, and a substituent on the carbon backbone of the alcohol, not only the intermediate group between carbonyl and phenyl, but also the intermediate group between the ester functional group and the location of the substituted carbon can significantly impact the properties and performance of the base stock.

The C21-alcohol phenylpropanoate ester (Example B5) has very similar kinematic viscosity at 100° C. to low viscosity PAO 3.6 (Example C1) but has much higher viscosity index (140 vs. 120) and much lower volatility (4.4 vs. 17). Similarly the C21-alcohol benzoate ester (Example B6) has very similar kinematic viscosity at 100° C. as low viscosity PAO 3.6 (Example C1) but has a much lower volatility (7.7 vs. 17). In base stock applications, aromatic functionality of benzoic or phenyl propionic ester have potential advantages in terms of thermo-oxidative stability and solvency (polarity). It is surprising that the C21-alcohol phenylpropanoate ester (Example B5) and C21-alcohol benzoate ester (Example B6) has very similar kinematic viscosity at 100° C. even though the molecular weight of propionate ester is much higher than benzoate ester (444.7 vs. 416.7).

The benzoate fluids can also be used as PVC plasticizers and in personal care applications.

The properties of selective gamma-branched C21-alcohol based propionate ester, similar to the C20-alcohol Guerbet alcohol based phenylpropanoate fluid, are better than benzoate esters with good KV100-Noack Volatility balance. However, the KV100-Noack Volatility balance of all these ester fluids are better than low viscosity hydrocarbon base stock, PAO3.6. Low volatility reduces evaporative and degradation-induced oil losses that are expected in the high-temperature, oxidative environment of an internal combustion engine. Moreover, the selective gamma-branched C21-alcohol can be available at a lower cost than the C20-alcohol Guerbet alcohol.

What is claimed is:

1. A compound having the following formula (F-I):

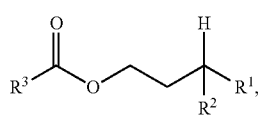

(F-I)

wherein $R^1$ and $R^2$ are independently each a C2 to C30 linear or branched alkyl group and wherein $R^1$ and $R^2$, taken together, comprise from 8 to 48 carbon atoms; and $R^3$ is a hydrocarbyl group.

2. The compound of claim 1, wherein $R^1$ and $R^2$ are independently each a linear alkyl group.

3. The compound of claim 1, wherein $R^1$ and $R^2$ are independently each a C2-C24 alkyl group.

4. The compound of claim 1, wherein the difference in total number of carbon atoms contained in $R^1$ and $R^2$ is two (2).

5. The compound of claim 1, wherein $R^2$ contains more carbon atoms than $R^1$, and $R^1$ contains 2, 4, 6, 8, 10, 12, 14, 16, 18, 20, or 22 carbon atoms in total.

6. The compound of claim 1, wherein $R^3$ is a linear or branched alkyl group, an aryl group, an arylalkyl group, an alkylaryl group, a cycloalkyl group, a cycloalkylalkyl group, or an alkylcycloalkyl group.

7. The compound of claim 6, wherein $R^3$ comprises 2 to 24 carbon atoms in total.

8. The compound of claim 1, wherein $R^3$ is an aryl group or alkylaryl group selected from phenyl, 1-naphthyl, 2-naphthyl, 3-naphthyl, phenanthryls, and alkylated derivatives thereof comprising one or more linear or branched alkyl substituents.

9. The compound of claim 1, wherein $R^3$ is selected from: methyl, ethyl, n-propyl, n-butyl, n-pentyl, n-hexyl, n-heptyl, n-octyl, n-decyl, n-dodecyl, n-tetradecyl, n-hexadecyl, n-octadecyl, n-icosyl, n-docosyl, n-tetracosyl, phenyl, 1-phenylmethyl, 2-phenylmethyl, 3-phenylpropyl, 4-phenylbutyl, 5-phenylpentyl, 6-phenylhexyl, 7-phenylheptyl, 8-phenyloctyl, 9-phenylnonyl, and 10-phenyldecyl.

10. A compound having the following formula (F-I):

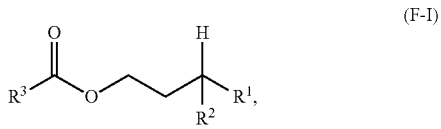

(F-I)

wherein $R^1$ and $R^2$ are independently each a C2 to C30 linear or branched alkyl group; and $R^3$ is a hydrocarbyl group, and wherein the compound is selected from the group consisting of:
3-ethylheptyl acetate;
3-ethylheptyl propanoate;
3-ethylheptyl butanoate;
3-ethylheptyl pentanoate;
3-ethylheptyl hexanoate;
3-ethylheptyl octanoate;
3-ethylheptyl decanoate;
3-ethylheptyl dodecanoate;
3-ethylheptyl tetradecanoate;
3-ethylheptyl hexadecanoate;
3-ethylheptyl octadecanoate;
3-ethylheptyl icosanoate;
3-ethylheptyl 3-phenylpropanoate;
3-ethylheptyl 2-phenylacetate;
3-ethylheptyl benzoate;
3-propyloctyl acetate;
3-propyloctyl propanoate;
3-propyloctyl butanoate;
3-propyloctyl pentanoate;
3-propyloctyl hexanoate;

3-propyloctyl octanoate;
3-propyloctyl decanoate;
3-propyloctyl dodecanoate;
3-propyloctyl tetradecanoate;
3-propyloctyl hexadecanoate;
3-propyloctyl octadecanoate;
3-propyloctyl icosanoate;
3-propyloctyl 3-phenylpropanoate;
3-propyloctyl 2-phenylacetate;
3-propyloctyl benzoate;
3-butylnonyl acetate;
3-butylnonyl propanoate;
3-butylnonyl butanoate;
3-butylnonyl pentanoate;
3-butylnonyl hexanoate;
3-butylnonyl octanoate;
3-butylnonyl decanoate;
3-butylnonyl dodecanoate;
3-butylnonyl tetradecanoate;
3-butylnonyl hexadecanoate;
3-butylnonyl octadecanoate;
3-butylnonyl icosanoate;
3-butylnonyl 3-phenylpropanoate;
3-butylnonyl 2-phenylacetate;
3-butylnonyl benzoate;
3-hexylundecyl acetate;
3-hexylundecyl propanoate;
3-hexylundecyl butanoate;
3-hexylundecyl pentanoate;
3-hexylundecyl hexanoate;
3-hexylundecyl octanoate;
3-hexylundecyl decanoate;
3-hexylundecyl dodecanoate;
3-hexylundecyl tetradecanoate;
3-hexylundecyl hexadecanoate;
3-hexylundecyl octadecanoate;
3-hexylundecyl icosanoate;
3-hexylundecyl 3-phenylpropanoate;
3-hexylundecyl 2-phenylacetate;
3-hexylundecyl benzoate;
3-octyltridecyl acetate;
3-octyltridecyl propanoate;
3-octyltridecyl butanoate;
3-octyltridecyl pentanoate;
3-octyltridecyl hexanoate;
3-octyltridecyl octanoate;
3-octyltridecyl decanoate;
3-octyltridecyl dodecanoate;
3-octyltridecyl tetradecanoate;
3-octyltridecyl hexadecanoate;
3-octyltridecyl octadecanoate;
3-octyltridecyl icosanoate;
3-octyltridecyl 3-phenylpropanoate;
3-octyltridecyl 2-phenylacetate;
3-octyltridecyl benzoate;
3-decylpentadecyl acetate;
3-decylpentadecyl propanoate;
3-decylpentadecyl butanoate;
3-decylpentadecyl pentanoate;
3-decylpentadecyl hexanoate;
3-decylpentadecyl octanoate;
3-decylpentadecyl decanoate;
3-decylpentadecyl dodecanoate;
3-decylpentadecyl tetradecanoate;
3-decylpentadecyl hexadecanoate;
3-decylpentadecyl octadecanoate;
3-decylpentadecyl icosanoate;
3-decylpentadecyl 3-phenylpropanoate;
3-decylpentadecyl 2-phenylacetate;
3-decylpentadecyl benzoate;
3-dodecylheptadecyl acetate;
3-dodecylheptadecyl propanoate;
3-dodecylheptadecyl butanoate;
3-dodecylheptadecyl pentanoate;
3-dodecylheptadecyl hexanoate;
3-dodecylheptadecyl octanoate;
3-dodecylheptadecyl decanoate;
3-dodecylheptadecyl dodecanoate;
3-dodecylheptadecyl tetradecanoate;
3-dodecylheptadecyl hexadecanoate;
3-dodecylheptadecyl octadecanoate;
3-dodecylheptadecyl icosanoate;
3-dodecylheptadecyl 3-phenylpropanoate;
3-dodecylheptadecyl 2-phenylacetate; and
3-dodecylheptadecyl benzoate.

11. A lubricating oil composition comprising a compound of claim 1.

12. The lubricating oil composition of claim 11, which is a lubricating oil base stock.

13. The lubricating oil composition of claim 12, which consists essentially of one or more compounds of formula (F-I).

14. The lubricating oil composition of claim 12, having a kinematic viscosity at 100° C. as determined pursuant to ASTM D445 in the range from 1 to 40 cSt.

15. The lubricating oil composition of claim 12, which is a lubricating oil formulation comprising a compound of any of claims 1 to 11 as a first base stock.

16. The lubricating oil formulation of claim 15, wherein the concentration of the first base stock, based on the total weight of the lubricant formulation, is in the range from 5 to 95 wt %.

17. The lubricating oil composition of claim 16, further comprising an additive and a second base stock selected from Group I, II, III, IV, and V base stocks.

18. A process for making a compound having the following formula (F-I) or a lubricating oil base stock comprising a compound having formula (F-I):

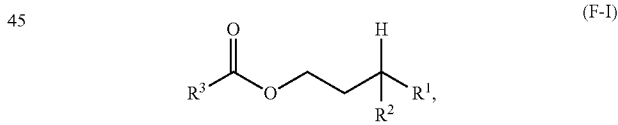

(F-I)

wherein $R^1$ and $R^2$ are independently each a C2 to C30 linear or branched alkyl group
wherein $R^1$ and $R^2$, taken together, comprise from 8 to 48 carbon atoms; and
$R^3$ is a hydrocarbyl group;
the method comprising:
reacting an acid having a formula (F-II) or an anhydride thereof having a formula (F-III) below with an alcohol having a formula (F-IV) below in the presence of an acid catalyst to obtain a reaction mixture:

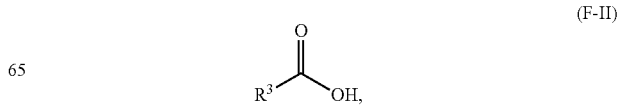

(F-II)

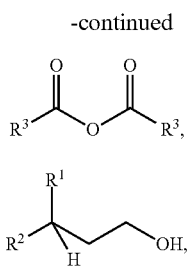

and
obtaining the compound or the lubricating oil base stock from the reaction mixture.

19. The process of claim 18, wherein $R^1$ and $R^2$ are independently each a C2 to C24 linear alkyl group.

20. The process of claim 18, wherein $R^3$ is a linear or branched alkyl group, an aryl group, an arylalkyl group, an alkylaryl group, a cycloalkyl group, a cycloalkylalkyl group, or an alkylcycloalkyl group.

21. The process of claim 18, wherein $R^3$ is an aryl group or alkylaryl group selected from phenyl, 1-naphthyl, 2-naphthyl, 3-naphthyl, phenanthryls, and alkylated derivatives thereof comprising one or more linear or branched alkyl substituents.

22. The process of claim 18, wherein $R^3$ is selected from: methyl, ethyl, n-propyl, n-butyl, n-pentyl, n-hexyl, n-heptyl, n-octyl, n-decyl, n-dodecyl, n-tetradecyl, n-hexadecyl, n-octadecyl, n-icosyl, n-docosyl, n-tetracosyl, phenyl, 1-phenylmethyl, 2-phenylmethyl, 3-phenylpropyl, 4-phenylbutyl, 5-phenylpentyl, 6-phenylhexyl, 7-phenylheptyl, 8-phenyloctyl, 9-phenylnonyl, and 10-phenyldecyl.

23. The process of claim 18, wherein the acid catalyst is selected from p-toluenesulfonic acid monohydride (PTSA), titanium isopropoxide and sulfuric acid.

24. The compound of claim 10, which is selected from the following:
3-propyloctyl acetate;
3-propyloctyl propanoate;
3-propyloctyl butanoate;
3-propyloctyl pentanoate;
3-propyloctyl hexanoate;
3-propyloctyl octanoate;
3-propyloctyl decanoate;
3-propyloctyl dodecanoate;
3-propyloctyl tetradecanoate;
3-propyloctyl hexadecanoate;
3-propyloctyl octadecanoate;
3-propyloctyl icosanoate;
3-propyloctyl 3-phenylpropanoate;
3-propyloctyl 2-phenylacetate;
3-propyloctyl benzoate;
3-butylnonyl acetate;
3-butylnonyl propanoate;
3-butylnonyl butanoate;
3-butylnonyl pentanoate;
3-butylnonyl hexanoate;
3-butylnonyl octanoate;
3-butylnonyl decanoate;
3-butylnonyl dodecanoate;
3-butylnonyl tetradecanoate;
3-butylnonyl hexadecanoate;
3-butylnonyl octadecanoate;
3-butylnonyl icosanoate;
3-butylnonyl 3-phenylpropanoate;
3-butylnonyl 2-phenylacetate;
3-butylnonyl benzoate;
3-hexylundecyl acetate;
3-hexylundecyl propanoate;
3-hexylundecyl butanoate;
3-hexylundecyl pentanoate;
3-hexylundecyl hexanoate;
3-hexylundecyl octanoate;
3-hexylundecyl decanoate;
3-hexylundecyl dodecanoate;
3-hexylundecyl tetradecanoate;
3-hexylundecyl hexadecanoate;
3-hexylundecyl octadecanoate;
3-hexylundecyl icosanoate;
3-hexylundecyl 3-phenylpropanoate;
3-hexylundecyl 2-phenylacetate;
3-hexylundecyl benzoate;
3-octyltridecyl acetate;
3-octyltridecyl propanoate;
3-octyltridecyl butanoate;
3-octyltridecyl pentanoate;
3-octyltridecyl hexanoate;
3-octyltridecyl octanoate;
3-octyltridecyl decanoate;
3-octyltridecyl dodecanoate;
3-octyltridecyl tetradecanoate;
3-octyltridecyl hexadecanoate;
3-octyltridecyl octadecanoate;
3-octyltridecyl icosanoate;
3-octyltridecyl 3-phenylpropanoate;
3-octyltridecyl 2-phenylacetate;
3-octyltridecyl benzoate;
3-decylpentadecyl acetate;
3-decylpentadecyl propanoate;
3-decylpentadecyl butanoate;
3-decylpentadecyl pentanoate;
3-decylpentadecyl hexanoate;
3-decylpentadecyl octanoate;
3-decylpentadecyl decanoate;
3-decylpentadecyl dodecanoate;
3-decylpentadecyl tetradecanoate;
3-decylpentadecyl hexadecanoate;
3-decylpentadecyl octadecanoate;
3-decylpentadecyl icosanoate;
3-decylpentadecyl 3-phenylpropanoate;
3-decylpentadecyl 2-phenylacetate;
3-decylpentadecyl benzoate;
3-dodecylheptadecyl acetate;
3-dodecylheptadecyl propanoate;
3-dodecylheptadecyl butanoate;
3-dodecylheptadecyl pentanoate;
3-dodecylheptadecyl hexanoate;
3-dodecylheptadecyl octanoate;
3-dodecylheptadecyl decanoate;
3-dodecylheptadecyl dodecanoate;
3-dodecylheptadecyl tetradecanoate;
3-dodecylheptadecyl hexadecanoate;
3-dodecylheptadecyl octadecanoate;
3-dodecylheptadecyl icosanoate;
3-dodecylheptadecyl 3-phenylpropanoate;
3-dodecylheptadecyl 2-phenylacetate; and
3-dodecylheptadecyl benzoate.

25. A compound having the following formula (F-I):

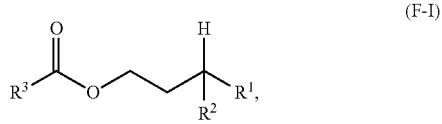
(F-I)

wherein $R^1$ and $R^2$ are independently each a C2 to C30 linear or branched alkyl group; and $R^3$ is an aryl group or alkylaryl group selected from phenyl, 1-naphthyl, 2-naphthyl, 3-naphthyl, phenanthryls, and alkylated derivatives thereof comprising one or more linear or branched alkyl substituents.

26. A process for making a compound having the following formula (F-I) or a lubricating oil base stock comprising a compound having formula (F-I):

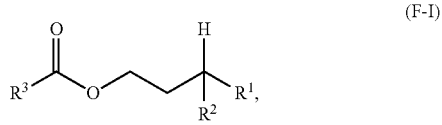
(F-I)

wherein $R^1$ and $R^2$ are independently each a C2 to C30 linear or branched alkyl group;

$R^3$ is an aryl group or alkylaryl group selected from phenyl, 1-naphthyl, 2-naphthyl, 3-naphthyl, phenanthryls, and alkylated derivatives thereof comprising one or more linear or branched alkyl substituents;

the method comprising:

reacting an acid having a formula (F-II) or an anhydride thereof having a formula (F-III) below with an alcohol having a formula (F-IV) below in the presence of an acid catalyst to obtain a reaction mixture:

(F-II)

(F-III)

(F-IV)

and obtaining the compound or the lubricating oil base stock from the reaction mixture.

* * * * *